United States Patent [19]

Wallace et al.

[11] Patent Number: 6,013,858
[45] Date of Patent: Jan. 11, 2000

[54] MOUSE LACKING HEART-MUSCLE ADENINE NUCLEOTIDE TRANSLOCATOR PROTEIN AND METHODS

[75] Inventors: Douglas C. Wallace, Atlanta; Brett H. Graham, Decatur; Grant R. MacGregor, Atlanta, all of Ga.

[73] Assignee: Emory University, Atlanta, Ga.

[21] Appl. No.: 08/961,871

[22] Filed: Oct. 31, 1997

Related U.S. Application Data

[60] Provisional application No. 60/030,017, Nov. 1, 1996.

[51] Int. Cl.$^7$ .......................... C12N 15/09; C12N 15/63; C12N 15/00; C12N 5/00

[52] U.S. Cl. ..................... 800/18; 800/3; 800/9; 800/21; 800/22; 800/25; 435/455; 435/463; 435/320.1; 435/325

[58] Field of Search ................. 800/2, 18, 3, 9, 800/21, 22, 25; 435/455, 463, 320.1, 325

[56] References Cited

PUBLICATIONS

Bakker, et al. (1993) "Deficiency of the adenine nucleotide translocator in muscle of a patient with myopathy and lactic acidosis: A new mitochondrial defect" *Pediatr. Res.* 33(4):412–417.

Bakker, et al. (1993) "Adenine nucleotide translocator deficiency in muscle: Potential therapeutic value of Vitamin E" *J. Inherit. Metab. Dis.* 16:548–552.

Barth, et al. (1992) "Ultrastructural quantitation of mitochondria and myofilaments in cardiac muscle from 10 different animal species including man" *J. Mol. Cell. Cardiol.* 24:669–681.

Battini, et al. (1987) "Molecular cloning of a cDNA for a human ADP/ATP carrier which is growth–regulated" *J. Biol. Chem.* 262(9):4355–4359.

Brown, M.D. and Wallace, D.C. (1994) "Molecular basis of mitochondrial DNA disease" *J. Bioenerg. Biomem.* 26(3):273–289.

DiMauro, et al. (1985) "Mitochondrial myopathies" *Ann. Neurol.* 17:521–538.

Ellison, et al. (1996) "Rapid evolution of human pseudoautosomal genes and their mouse homologs" *Mamm. Genome* 7:25–30.

Haraguichi, et al. (1993) "Genetic mapping of human heart–skeletal muscle adenine nucleotide translocator and its relationship to the facioscapulohumeral muscular dystrophy locus" *Genomics.* 16:479–485.

Hatchell and MacInnes (1973) "A quantitative analysis of the genetics of resting blood lacic acid levels in mice" *Genetics* 75:191–198.

Li, et al. (1989) "A human muscle adenine nucleotide translocator gene has four exons, is located on chromosome 4, and is differentially expressed" *J. Biol. Chem.* 264(24):13998–14004.

MacGregor, et al. (1995) "Tissue non–specific alkaline phosphatase is expressed in both embryonic and extraembryonic lineages during mouse embryogenesis but is not required for migration of primordial germ cells" *Development* 121:1487–1496.

Necklemann, et al. (1987) "cDNA sequence of a human skeletal muscle ADP/ATP translocator: Lack of a leader peptide, divergence from a fibroblast translocator cDNA, and coevolution with mitochondrial DNA genes" *Proc. Natl. Acad. Sci. USA.* 84:7580–7584.

Pfanner and Neupert (1987) "Distinct steps in the import of ADP/ATP carrier into mitochondria" *J. Biol. Chem.* 262(16):7528–7536.

Ramirez–Solis, et al. (1995) "Gene targeting in embryonic stem cells" *Guide to Techniques in Mouse Development* 225:855–878, eds. Wasserman, P.M. and DePamhlis, M.L., Academic Pres, San Diego, CA.

Servidei, et al. (1994) "Hereditary metabolic cardiomyopathies" *Adv. Pediatr.* 41:1–32.

Shinohara, Y., et al. (1993) "Isolation and characterization of cDNA clones and a genomic clone encoding rat mitochondrial adenine nucleotide translocator" *Biochim. Biophys. Acta.* 1152:193–196.

Shoffner and Wallace (1994) "Oxidative phosphorylation diseases" *The Metabolic and Molecular Bases of Inherited Disease,* Ch.46, pp.1535–1609, McGraw–Hill, 7th ed.

Soriano, et al. (1991) "Targeted disruption of the c–src Proto–Oncogene leads to osteopetrosis in mice" *Cell* 64:693–702.

Stepien, et al. (1992) "Differential expression of adenine nucleotide translocator isoforms in mammalian tissues and during muscle cell differentiation" *J. Biol. Chem.* 267(21):14592–14597.

Stewart, C.L. (1993) "Production of chimeras between embryonic stem cells and embryos" *Guide to Techniques in Mouse Development,* 225:823–855, eds. Wasserman, P.M. and De Pamphlis, M.L., Academic Press, San Diego, CA.

Thomson, S., et al. (1989) "Germ line transmission and expression of a corrected HPRT gene produced by gene targeting in embryonic stem cells" *Cell* 56:313–321.

(List continued on next page.)

*Primary Examiner*—Bruce R. Campell
*Assistant Examiner*—Jill D. Martin
*Attorney, Agent, or Firm*—Greenlee, Winner and Sullivan, PC

[57] ABSTRACT

Provided are transgenic mice genetically engineered for a deficiency of the heart-skeletal muscle isoform of the adenine nucleotide translocator protein (Ant1). These mice exhibit histological, biochemical and physiological signs of deficiency in oxidative phosphorylation and energy generation, and these mice provide the first animal model for mitochondrial myopathy and hypertrophic cardiomyopathy. This animal model is used in methods for testing compounds for therapeutic value in treating failure to exchange ATP and ADP across the mitochondrial inner membrane, OXPHOS deficiency and in treating cardiac hypertrophy.

8 Claims, 16 Drawing Sheets

PUBLICATIONS

Wallace, D.C. (1994) "Mitochondrial DNA mutations in diseases of energy metabolism" *J. Bioenerg. Biomem.* 26(3):241–250.

Wijmenga, et al. (1993) "The human skeletal muscle adenine nucleotide translocator gene maps to chromosome 4q35 in the region of the facioscapulohumeral musclular dystrophy locus" *Hum. Genet.* 92:198–203.

Fleay in 1944 (Augee,), 1992.

Charreau et al. (Transgenic researcch, (4) 223–34), Jul. 1996.

Ellison et al. (Mammalian Genome, (1) 25–30), Jan. 1996.

Hunter et al. (69th Scientific Sessions of the American Heart Association, Nov. 10–13, Circulation 94 (8 Suppl.) 1187). 1996.

Zimmer et al. (Biochemical and Biophysical Research Communications, 201 (2) 943–9), Jun. 15, 1994.

Kuroda et al. (J. Bacteriology, 177 (24) 7019–25), Dec. 1995.

Shastry B. (Experientia, 51 (11) 1028–39), Nov. 15, 1995.

Moreadith et al., J. Mol. Med., vol. 75, pp. 208–216, 1997.

Capecchi et al., Scientific American, vol. 270, No. 3, pp. 34–41, Mar. 1994.

MOUSE LACKING HEART-MUSCLE ADENINE NUCLEOTIDE TRANSLOCATOR PROTEIN AND METHODS

CROSS-REFERENCE TO RELATED APPLICATIONS

This application claims priority from United States Provisional Application No. 60/030,017, filed Nov. 1, 1996, which is incorporated by reference in its entirety.

ACKNOWLEDGEMENT OF FEDERAL RESEARCH SUPPORT

This invention was made, at least in part, with funding from the National Institutes of Health (Grant Nos. HL45572 and NS21328). Accordingly, the United States Government has certain rights in this invention.

BACKGROUND OF THE INVENTION

The field of the invention is in the area of transgenic mice, specifically, a transgenic mouse lacking the mitochondrial protein called heart-muscle adenine nucleotide translocator, and in the testing of genetic therapies and/or pharmaceuticals in animal model systems, particularly those genetic therapies and/or pharmaceuticals of benefit in protecting against or ameliorating mitochondrial myopathy and/or certain mitochondrial disease in a human or animal susceptible to or suffering from same.

Mitochondrial oxidative phosphorylation (OXPHOS) is a complex biochemical process central to aerobic energy metabolism. Oxidative energy (in the form of electrons donated by NADH or $FADH_2$) is transformed by the electron transport chain (Complexes I–IV) into a chemiosmotic gradient across the inner mitochondrial membrane that is utilized by ATP synthase (Complex V) to phosphorylate ADP, providing ATP as an energy source for the cell.

Heart-muscle adenine nucleotide translocator, encoded by the ANT1 locus, is the most abundant mitochondrial protein. ANT1 is encoded by a nuclear gene, and the functional unit is a 60 kDa homodimer embedded in the inner mitochondrial membrane. ANT plays a central role in OXPHOS by acting as a solute carrier which imports ADP from the cytosol into the mitochondrial matrix (to be phosphorylated by ATP synthase) and exports newly phosphorylated ATP from the matrix into the cytosol. Thus, it plays a critical role in energy metabolism. ANT exists in multiple isoforms in many species. In mammals, these ANT isoforms exhibit tissue-specific gene expression patterns (Stepien et al. (1992) *J. Biol. Chem.* 267:14592–14597 and hereinbelow). Ant1 is considered a heart/muscle specific isoform due to its predominant expression in cardiac and skeletal muscle.

Studies over the past 10 years linking mutations in mitochondrial DNA and human disease have supported a mitochondrial OXPHOS paradigm that hypothesizes defects in OXPHOS result in disease manifesting itself in tissues most dependent on oxidative metabolism (i.e., CNS, heart, skeletal muscle) [reviewed in Wallace, D.C. (1994) *J. Bioenerg. Biomem.* 26:241–250; Brown, M.D. and Wallace, D.C. (1994) *J. Bioenerg. Biomem.* 26:273–289]. A defect in ANT1 in three different facioscapulohumeral muscular dystrophy patients has been suggested by Wijmenga et al. (1993) *Hum. Genet.* 92:198–203.

In order to directly test this paradigm and to better understand the biological role of multiple ANT isoforms, the present inventors have made "knockout" mice lacking a functional Ant1 gene product.

Oxygen radical injury has been implicated in pulmonary oxygen toxicity, adult respiratory distress syndrome, bronchopulmonary dysplasia, sepsis syndrome and various ischemia-reperfusion syndromes including myocardial infarction, stroke, cardiopulmonary bypass, organ transplantation, necrotizing enterocolitis, acute renal tubular necrosis, among others. Oxygen radical damage can result from a disruption of mitochondrial energy generation, for example, when normal ATP/ADP exchange is blocked. Accumulated free radical damage has also been associated with the normal aging process.

SUMMARY OF THE INVENTION

The present invention provides a transgenic mouse which is an example of a model for tissue-specific mitochondrial disease caused by the inactivation of a nuclear gene encoding a tissue-specific isoform of a component of the oxidative phosphorylation pathway. As specifically exemplified herein, the invention provides a transgenic mouse which lacks the mitochondrial heart-skeletal muscle isoform (ANT1) of the adenine nucleotide translocator due to the inactivation of the nuclear gene on chromosome 8. The mouse which is homozygous for the inactivated ANT1 is designated Ant1 (–/–). Due to this deficiency in the ANT1 protein, these mice are chronically deficient in energy in affected tissues (especially heart and skeletal muscle). This mouse is useful as a model of conditions including, but not limited to, human mitochondrial disease, hypertrophic cardiomyopathy and myopathy, degenerative muscle disease, lactic acidosis, organic acidemias, and defects in energy generation. This mouse is also useful as an example of a broader class of mouse models for tissue-specific mitochondrial disease resulting from disruption of a tissue-specific isoform of a component of oxidative phosphorylation.

By about 6 months of age, the Ant1 (–/–) mice show symptoms of chronic energy deprivation, with muscle weakness, low strength and endurance in contrast to heterozygous Ant1 (–/–) and wild-type Ant1 (–/–) mice. Histological and ultrastructural examination of muscle tissue reveals characteristic ragged red fibers, and hyperproliferation of mitochondria. After about 6–12 months of age, the Ant1 (–/–) mice also develop lactic acidosis, organic acidemias and hypertrophic cardiomyopathy, the result of the heart's attempts to compensate for cardiac muscle weakness due to chronic energy deficiency.

The present invention further provides a model system in which to study the pathophysiology of mitochondrial disease resulting from chronic energy deficiency, for example, where ATP generated within the mitochondria cannot be exchanged for ADP outside the mitochondria or due to a defect in muscle mitochondrial cytochrome c oxidase. Without wishing to be bound by theory, it is believed that this Ant1 (–/–) mouse is also characterized by lower ATP production than in a normal mouse because inhibition of mitochondrial ATP/ADP exchange also inhibits the respiratory chain. Inhibition of the respiratory chain results in an increased NADH/NAD ratio, increased reduction of the respiratory chain, and increased oxygen radical (reactive oxygen species, ROS) production. Thus, with the passage of time, the Ant1 (–/–) mouse shows damage resulting from free radical activity in affected tissues, including the heart and skeletal muscle. The results are especially dramatic in tissues in which ANT2 is not expressed; these tissues include the basal ganglia and the external symptoms of ANT1 deficiency include severe motor malfunction. Evidence that oxygen radical damage is an important secondary component of the pathophysiology of ANT (–/–) mice is that the hearts of mutant mice show increased levels of mitochondrial DNA rearrangements by 5 to 7 months of age. Therefore, the Ant1 (−/−) mouse is useful as a model system in which to test potentially therapeutic free radical scavengers, antioxidants and/or bioenergetics-modifying compounds for use in the treatment of chronic energy deficiency, hypertrophic cardiomyopathy, myopathy, lactic acidosis, organic acidemias, and/or mitochondrial disease as well as to test genetic therapies to correct or to compensate in mitochondrial diseases. Candidate compounds for such testing include Coenzyme Q, ascorbic acid, menadione, succinate, superoxide dismutase (SOD), catalase chemical mimics and protected ATP analogs. The Ant1 (−/−) mouse is also a model system for testing compounds which increase or mediate exchange of ATP and ADP across the mitochondrial membrane independent of the ANT1 protein.

The present invention further provides a method for testing compounds of potential pharmaceutical use in protecting against or ameliorating the effects of the inability of the mitochondria to exchange internal ATP for external ADP in the aforementioned transgenic mouse. For example, a method for identifying compounds which mediate the exchange of ATP and ADP across the mitochondrial membranes independent of the ANT1 protein. Those compounds which mediate the exchange of ATP/ADP across biological membranes, particularly across the mitochondrial membranes, and also, the present invention provides a method for testing the therapeutic potential of compounds that increase ATP production through secondary sources such as glycolysis, compounds which alter the oxidation production state of the cell or tissue and compensate for elevated NADH/NAD, and GSH/GSSG ratios in cells and tissues, or compounds which reduce lactate production such as dichloroacetate. Hence, this model will permit identification of therapeutics which may be effective in treating lactic acidosis, organic acidemias, hypertrophic cardiomyopathy, mitochondrial myopathy and poor endurance. Where the test compound is effective for mediating ATP/ADP exchange, increasing ATP production, altering the redox state, or changing the conversion of pyruvate to lactate, endurance and muscle performance, cardiac output, tissue histology and mitochondrial ultrastructure, and serum lactic acid, alanine and organic acid (for example, Krebs cycle intermediates) levels are substantially equivalent to that of an untreated normal Ant1 (+/+) mouse.

The present method comprises the step of administering a potentially therapeutic compound or gene therapy composition to a homozygous Ant1-deficient mouse, monitoring clinical condition of the treated mouse in comparison to an untreated (control) homozygous Ant1-normal mouse, monitoring the controls and the treated mice for symptoms of central nervous system damage, cardiac structdure and performance, and mitochondrial myopathy, and identifying compounds of potential use in therapy as those which prolong good clinical condition and/or which delay or prevent symptoms of energy deficiency in the skeletal and heart muscle amd prevent or reduce the lactic acidosis and/or organic acidemias in blood or serum.

The present invention also provides a method for the testing of compounds or gene therapies for use in preventing or reducing chronic energy deficiency, for example, the development of ragged red muscle fibers or hyperproliferation of mitochondria in tissue samples. Such potentially useful compounds are identified as preventing, delaying or reducing overt symptoms of chronic energy deficiency in the homozygous ANT1-deficient mouse. Additionally, the present animal model system and methods can be used to identify compounds useful in treating or preventing damage associated with chronic energy deficiency in medical conditions including, but not limited to, organic acidemias, lactdic acidosis, poor endurance, mitochondrial myopathy and hypertrophic cardiomyopathy.

The present animal model also permits the testing of potentially useful gene therapies or pharmaceutical compositions which stimulate the utilization of alternative energy sources in the body, which compensate for (or prevent) metabolic acidosis and which reestablish redox balance.

The present animal model further permits testing the efficacy of various gene therapy approaches for treating mitochondrial disease resulting from mutations in nuclear genes.

The present animal model provides a system for testing the effectivness of potential gene therapy delivery systems which are designed to deliver genes specifically to skeletal muscle or heart. This is because these animals have marked muscle and heart conditions with numerous associated sequelae, which would be readily ameliorated by introduction of the small ANT1 gene or cDNA. Hence, this sytem will be ideal for rapidly screening the effectiveness of nucleic acid delivery systems to the muscle and heart.

Finally, the ANT1 (−/−) animal provides a model system for fascioscapular humeral muscular dystropy.

BRIEF DESCRIPTION OF THE DRAWINGS

In FIG. 6A, the heart is blue for the Ant1 (+/−) animals and unstained for the Ant1 (+/+) animals. FIG. 6B shows results or skeletal muscle samples of Ant1 (+/−) (stained) and for Ant1 (+/+) animals (unstained). FIG.

6C is the results of activity staining a coronal section of the brain of an Ant1 (+/−) animal, with readily apparent regional staining of the tissue.

Figure 7A:
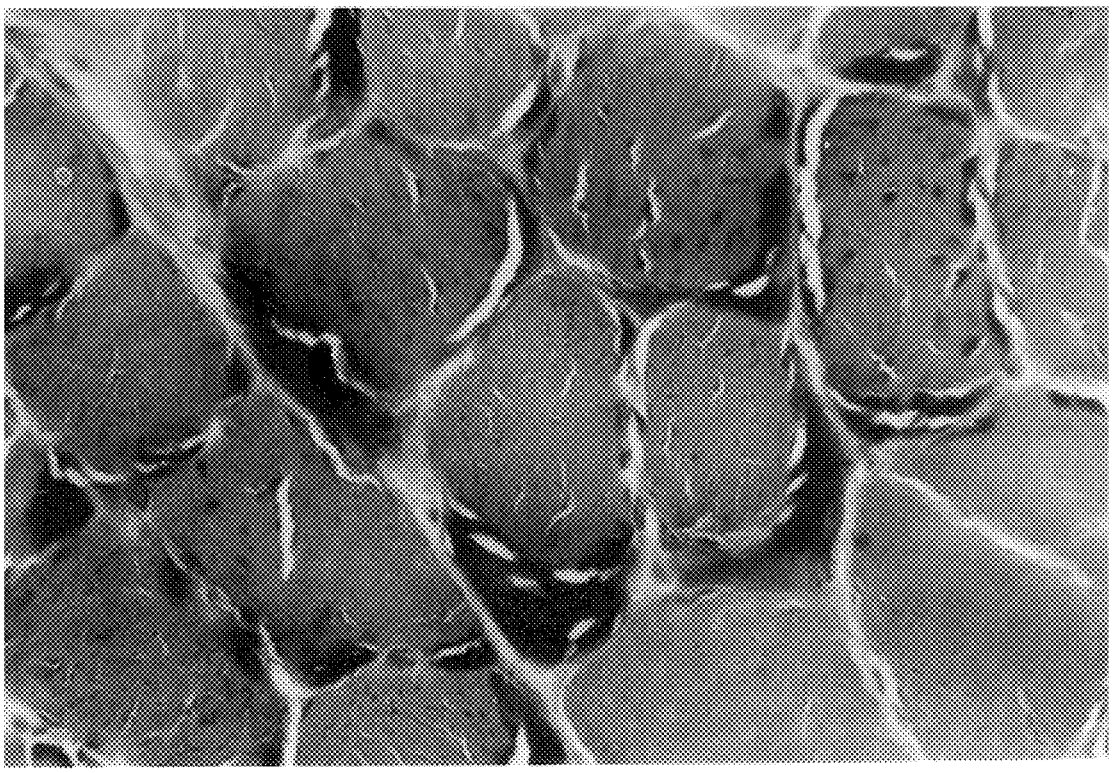
Figure 7B:
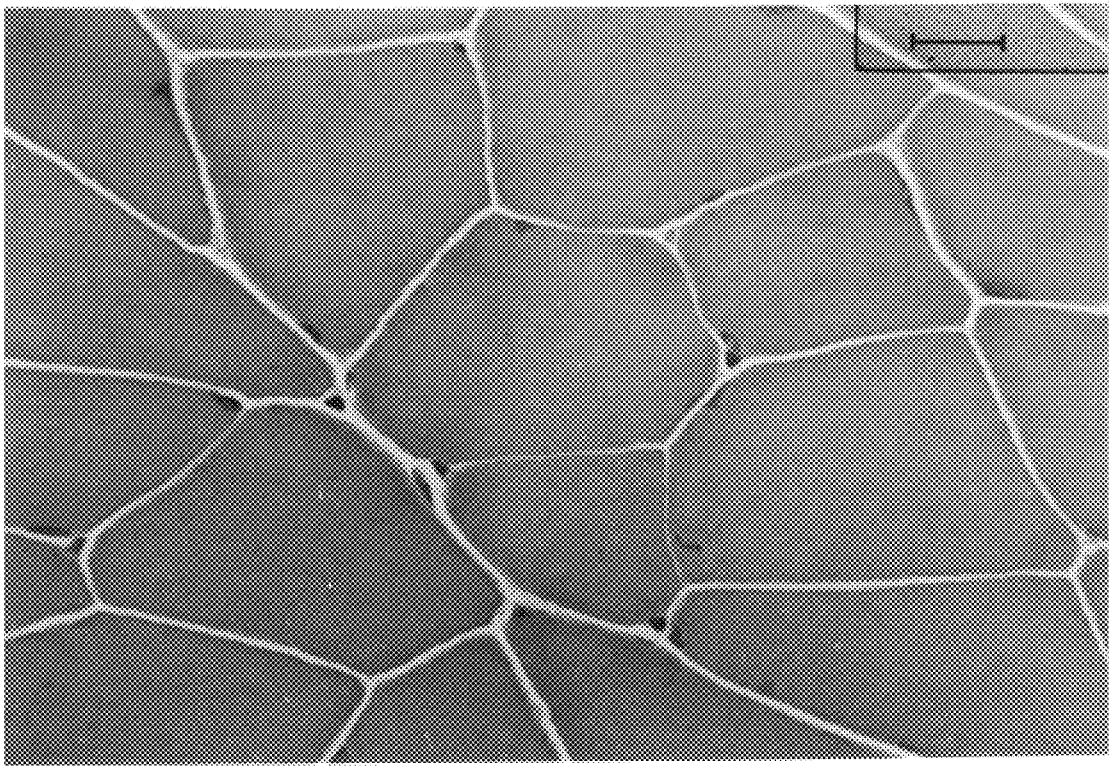

FIG. 7A–7B illustrates the results of Gomori-modified trichome staining of frozen muscle sections: FIG. 7A, Ant1 (−/−) animals show ragged red muscle fibers; FIG. 7B, Ant1 (+/+) animals with normal muscle.

Figure 8A:
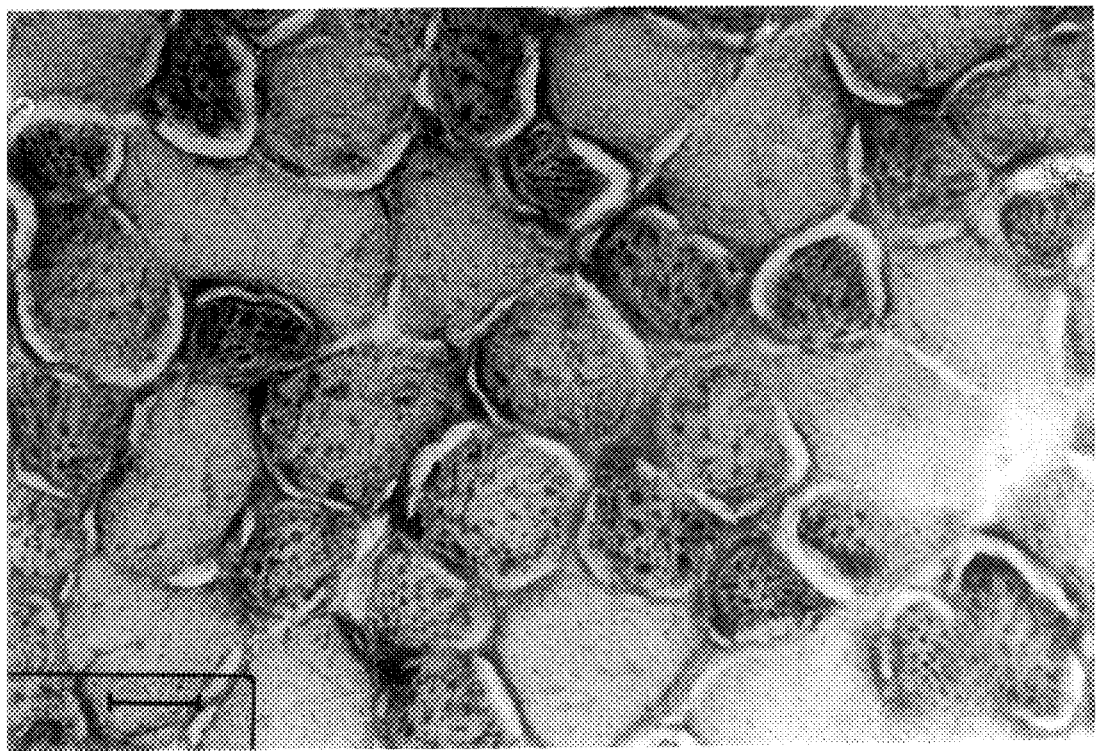
Figure 8B:
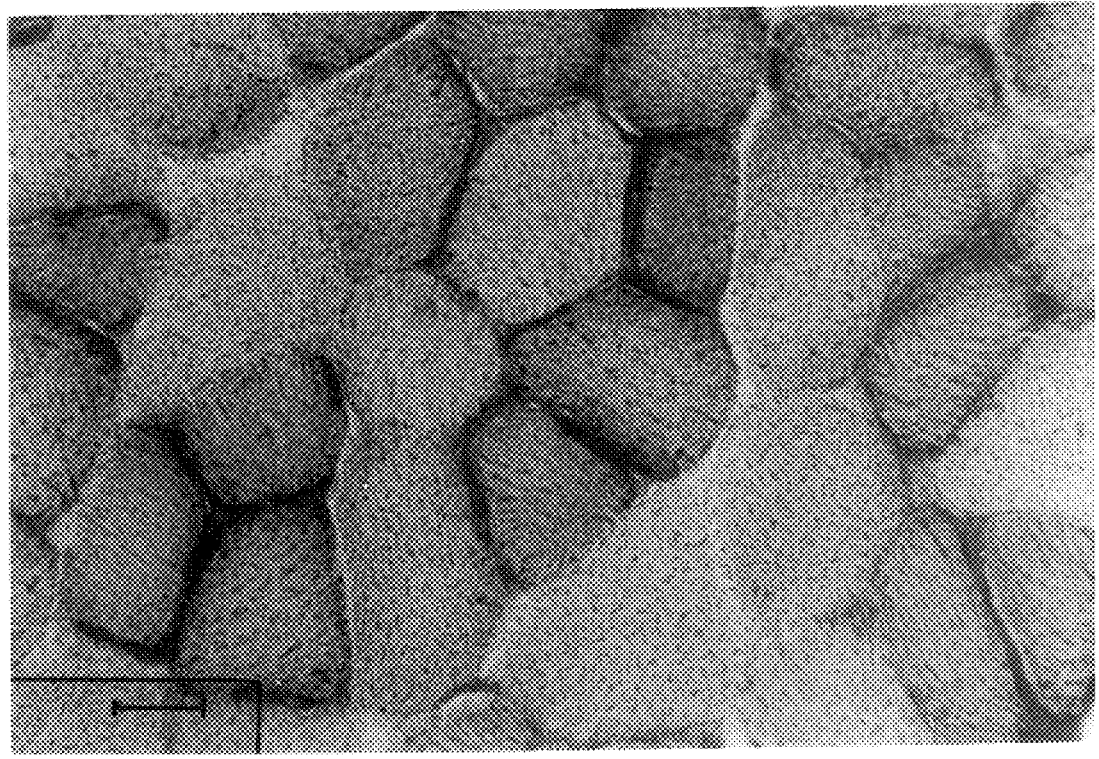

FIG. 8A–8B shows the results of succinate dehydrogenase staining of frozen muscle sections: FIG. 8A, Ant1 (−/−) animals; FIG. 8B, Ant1 (+/+) animals.

Figure 9A:
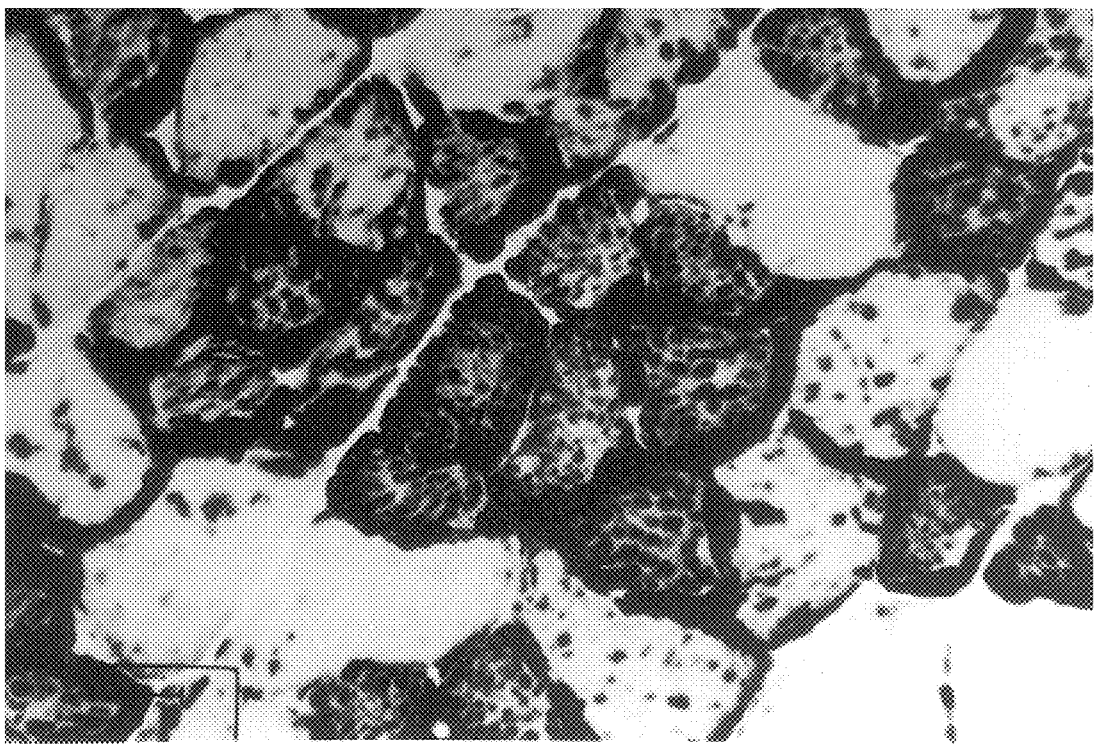
Figure 9B:
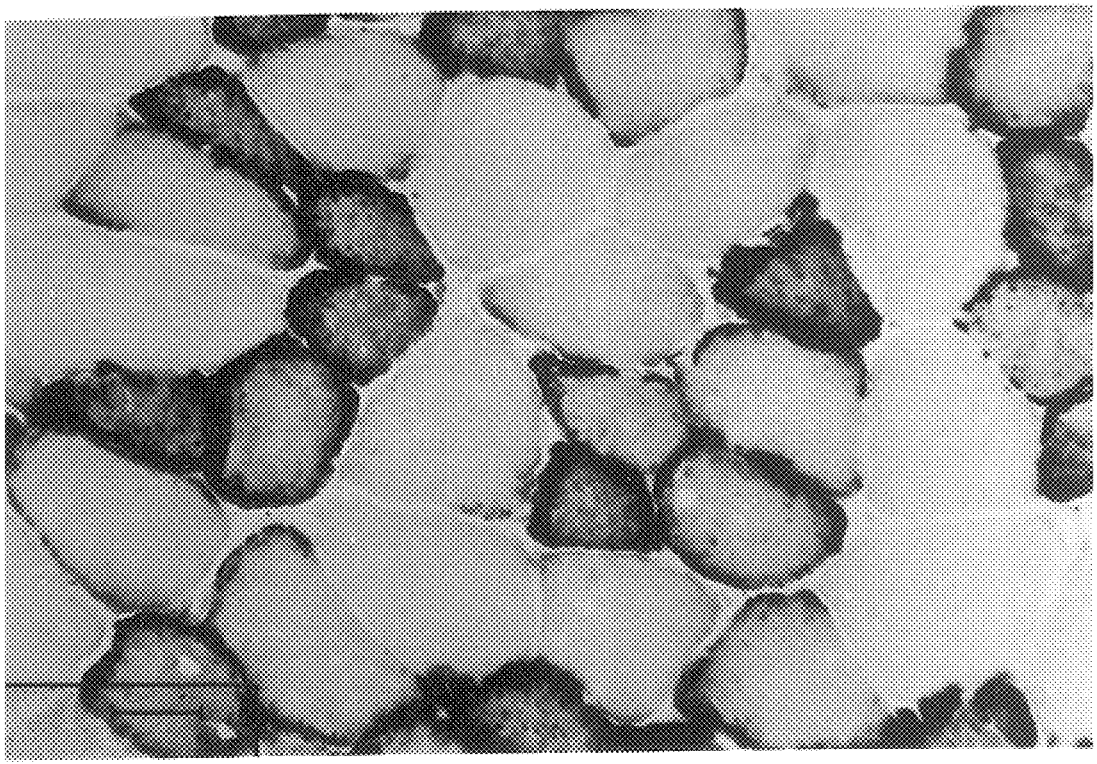

FIG. 9A–9B shows the results of cytochrome c oxidase staining of frozen muscle sections: FIG. 9A, Ant1 (−/−) animals; FIG. 9B, Ant1 (+/+) animals.

Figure 10A:
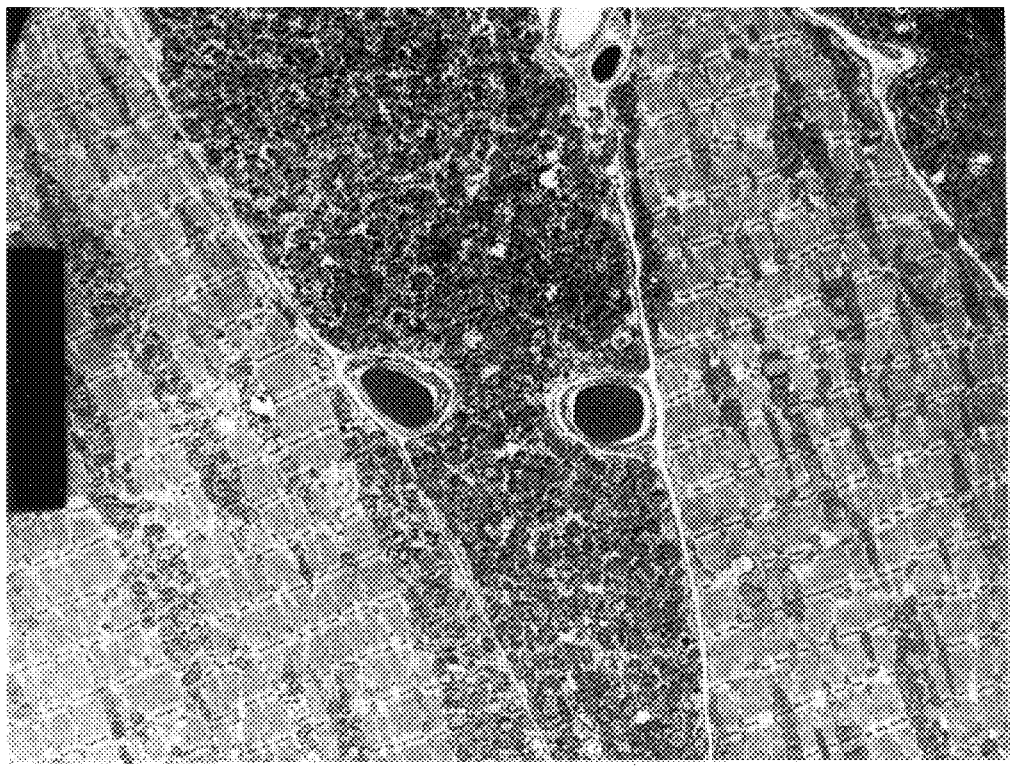
Figure 10B:
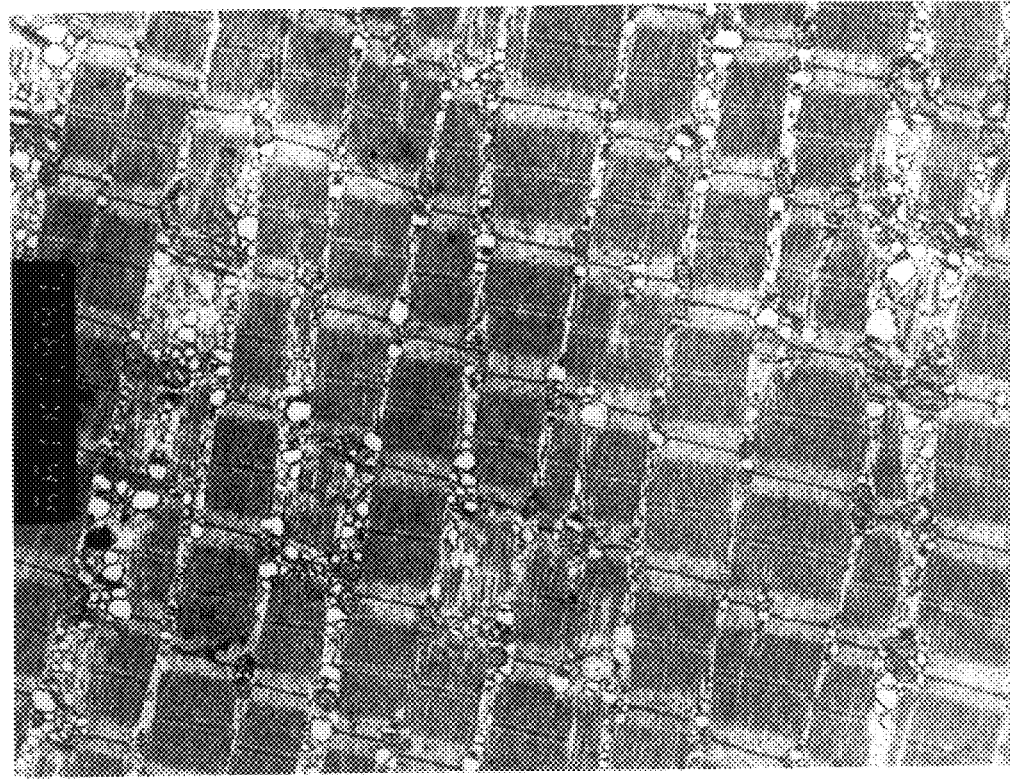

FIG. 10A–10B are reproductions of electron micrographs of skeletal muscle sections from the Ant1 (−/−) (FIG. 10A) and the normal Ant1 (+/+) mice.

Figure 11:
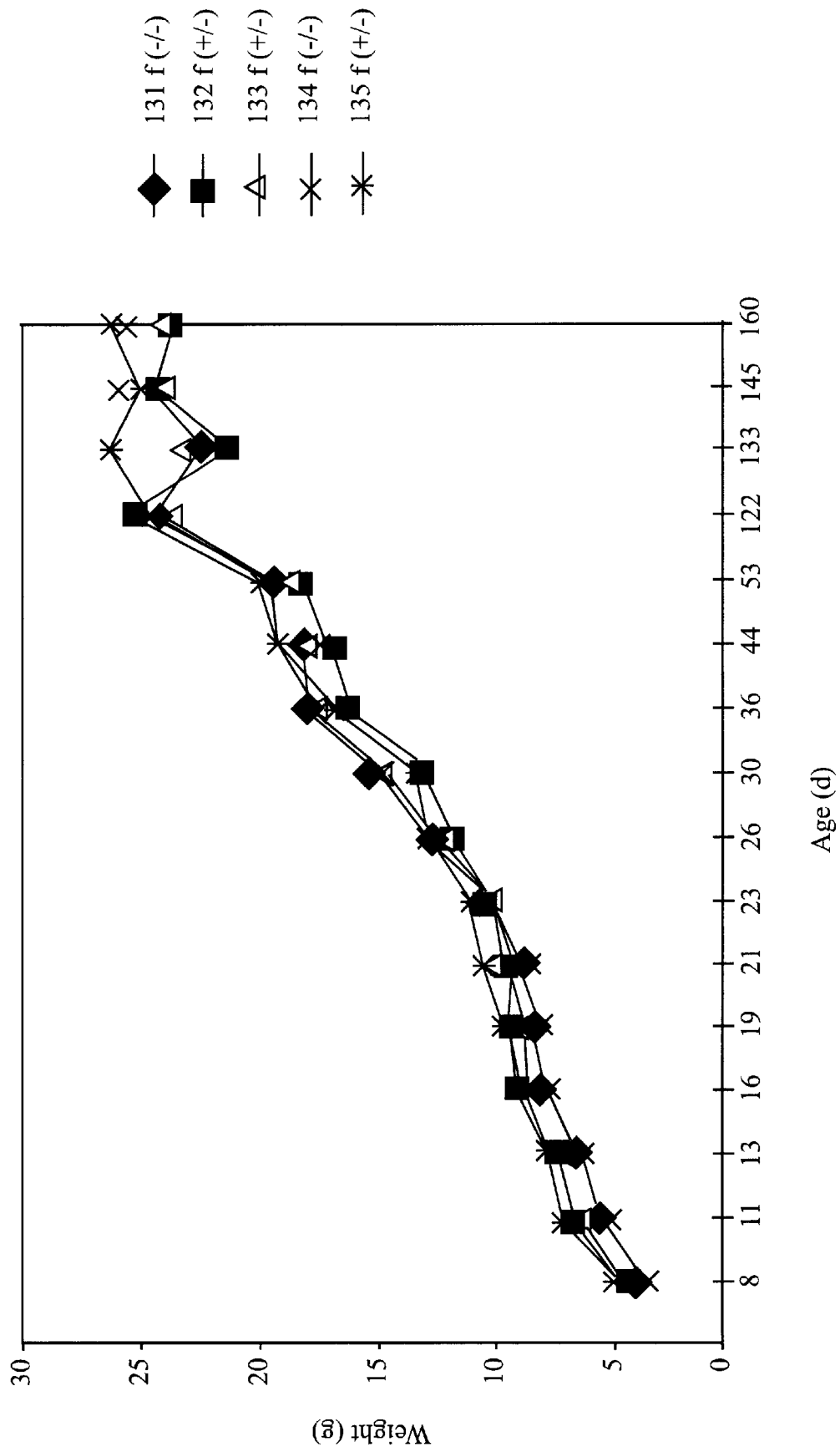

FIG. 11 shows weight (in grams) versus time (in days) for transgenic mice which are Ant1 (+/−) and (−/−).

Figure 12:
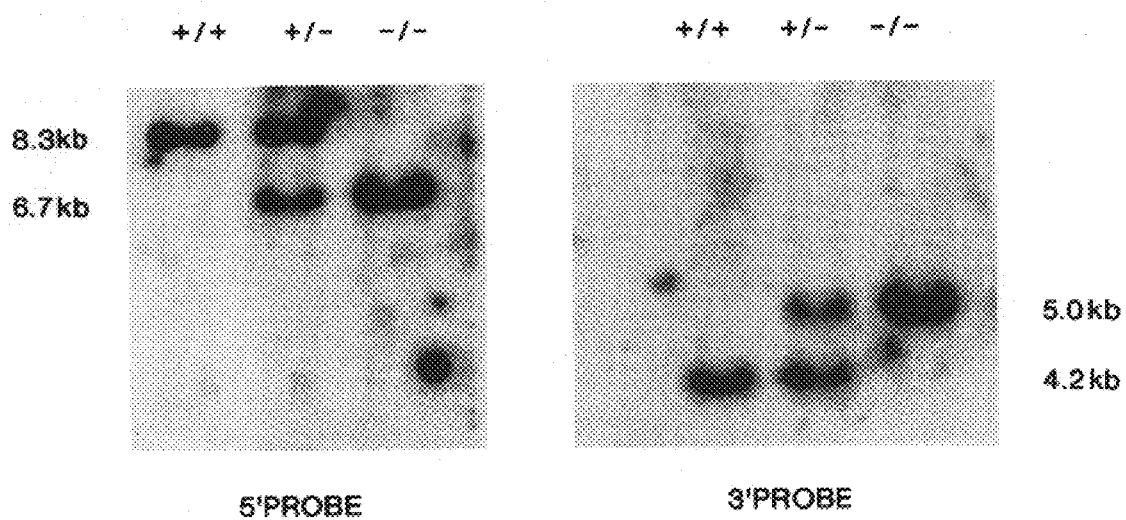

FIG. 12 is a reproduction of an autoradiogram of Ant1-directed Southern hybridization analysis of Ant1 wild-type (+/+), heteerozygous (+/−) and homozygous (−/−) mutant mice.

Figure 13:
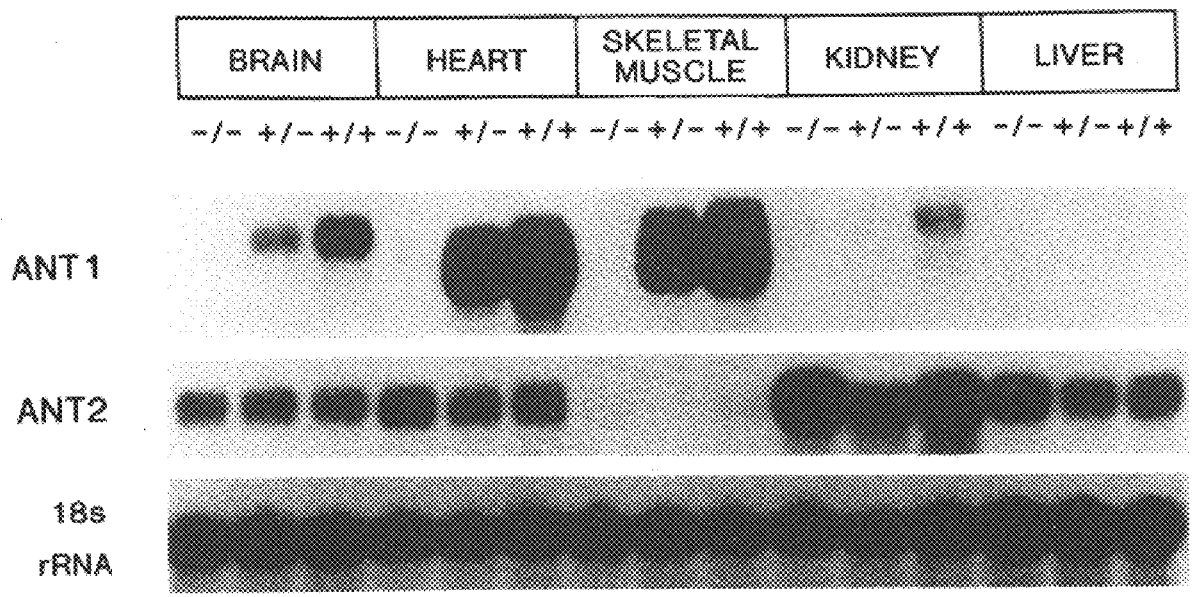

FIG. 13 illustrates Northern hybridization analyses carried out for wild-type (+/+) and Ant1-PGKneo (+/−) and (−/−) mice using RNA isolated from certain tissues and organs.

Figure 14A:
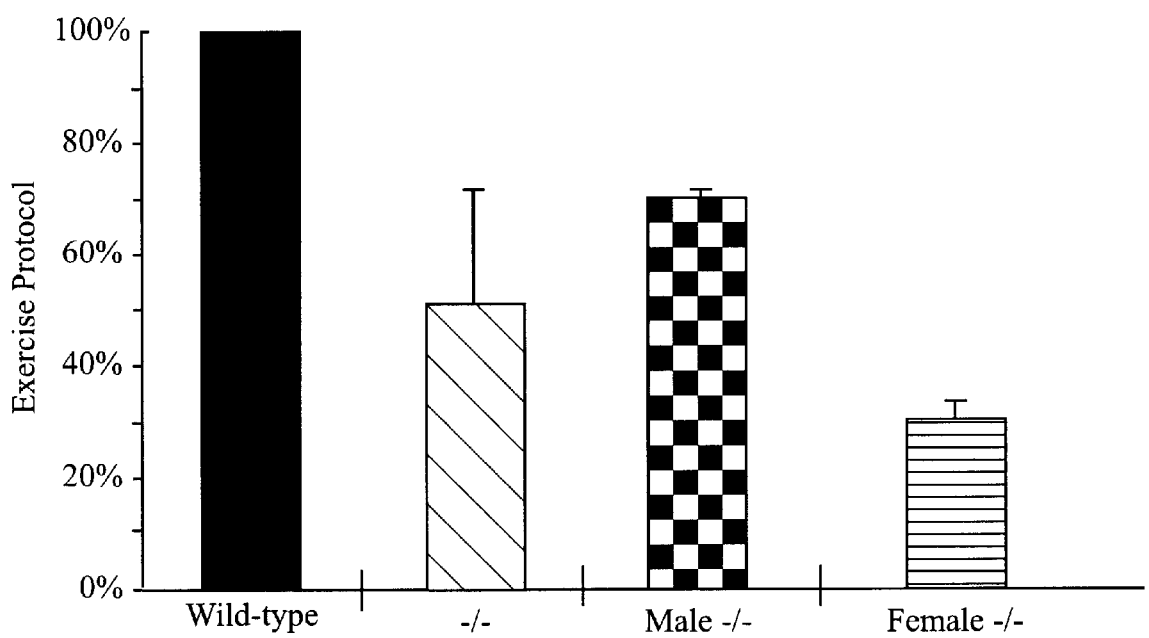
Figure 14B:
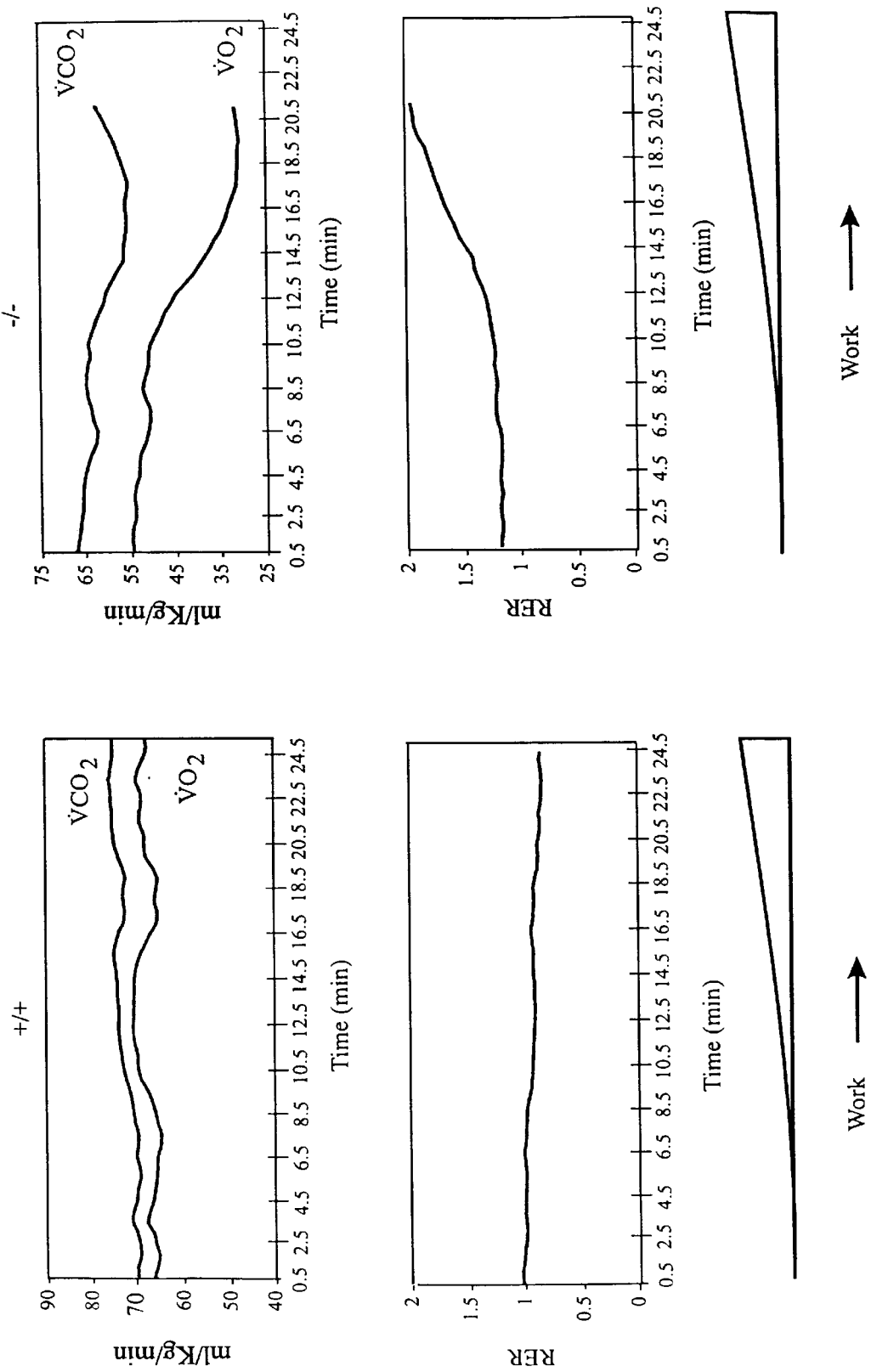

FIGS. 14A–14B illustrate the results of exercise stress testing in the wild-type, heterozygous Ant1 (+/−) and Ant1 (−/−) mice. FIG. 14A is a bar graph showing the average proportion (%) of an exercise protocol involving incremental increases in work that could be completed by normal (n=6) and mutant (n=6) mice. The normal animals (wild-type and heterozygous) (blackbar) showed no detectable fatigue during the protocol. The homozygous (−/−) animals, including those of both sexes (diagonal-lined bar), collapsed, on average, halfway through the protocol. The mutant males (n=3, checkered bar) could endure more of the protocol than the mutant females (n=3, horizontal-lined bar). The error bars represent ±1 standard deviation from the mean. FIG. 14B depicts typical respirometry measurements during an exercise stress test for both a normal (+/+) and a mutant (−/−) male mouse. The top graphs show the rates (ml/Kg/min) of oxygen consumption ($Vo_2$) and carbon dioxide production ($Vco_2$) during the exercise protocol. The bottom graphs display the ratio of $Vco_2$ to $Vo_2$, the respiratory exchange ratio (RER). The diagrams below the graphs depict the increasing workload required during the test, with increasing height of the line indicating a greater work load. Note that the time course of the experiment is shorter for the mutant mouse, as the onset of fatigue necessitated premature termination of the exercise test.

DETAILED DESCRIPTION OF THE INVENTION

Figure 1:
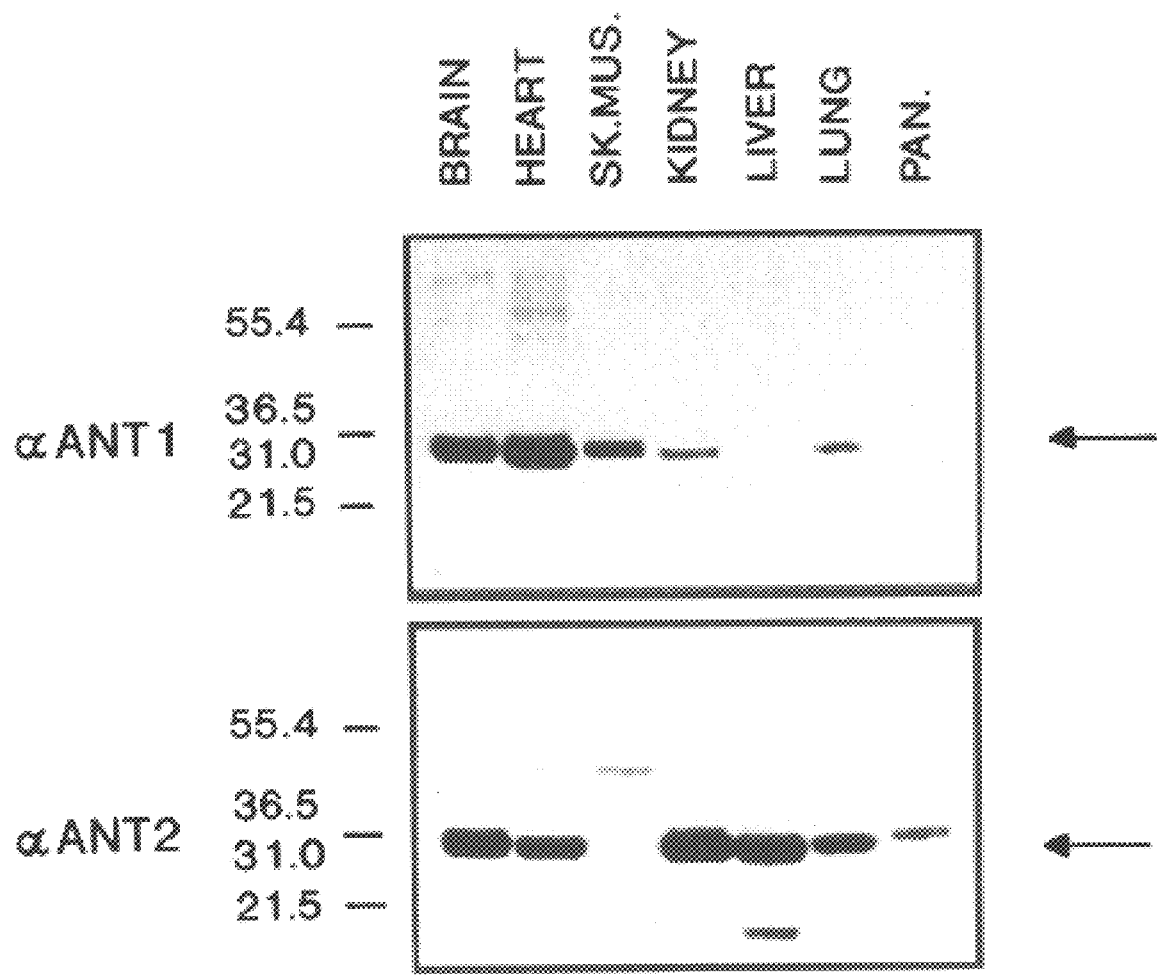
FIG. 1 is a reproduction of Western blot analysis of mouse ANT1 expression. Polyclonal antibodies were prepared to the N-terminal peptides of ANT1 and ANT2, shown on the far right. These antibodies were reacted against total tissue protein after size separation of proteins by polyacrylamide gel electrophoresis. The expression of ANT1 and ANT2 in brain, heart, skeletal muscle (SK MUS), kidney, liver, lung and pancreas (PAN) mice is shown.

The Adenine Nucleotide Translocator Protein mediates the exchange of ATP produced during oxidative phosphorylation and ADP generated by hydrolysis of ATP outside the mitochondrion across mitochondrial membranes. There are multiple isoforms in mammals, including two isoforms in the mouse. ANT1 is the isoform of this protein which is expressed in the heart, skeletal muscle and brain. ANT2 is expressed in all tissues, including brain, but at very low levels in skeletal muscle. See e.g., Stepien et al. (1992) *J. Biol. Chem.* 267:14592–14597. The present inventors have studied tissue-specific expression using ANT isoform specific antibodies generated in response to the corresponding peptide antigens. See FIG. 1. The amino acid sequence of the oligopeptide antigen used to prepare ANT1-specific antibody is MGDQALSFLKDFLAG (SEQ ID NO:1); the amino acid sequence of the oligopeptide antigen used to prepare ANT2-specific antibody is MTDAAVSFAKDFLAG (SEQ ID NO:2).

Northern analysis of ANT isoform expression in the adult 129/Sv mouse (FIG. 12) reveals that Ant1 is most strongly expressed in heart and skeletal muscle, with significant expression in brain, kidney, eye, lung, and testes. Ant2 is most strongly expressed in kidney, with low expression also in brain, heart, intestine, liver, and eye, and very low expression in skeletal muscle. See also FIG. 1 for immunoblot data.

Figure 3:
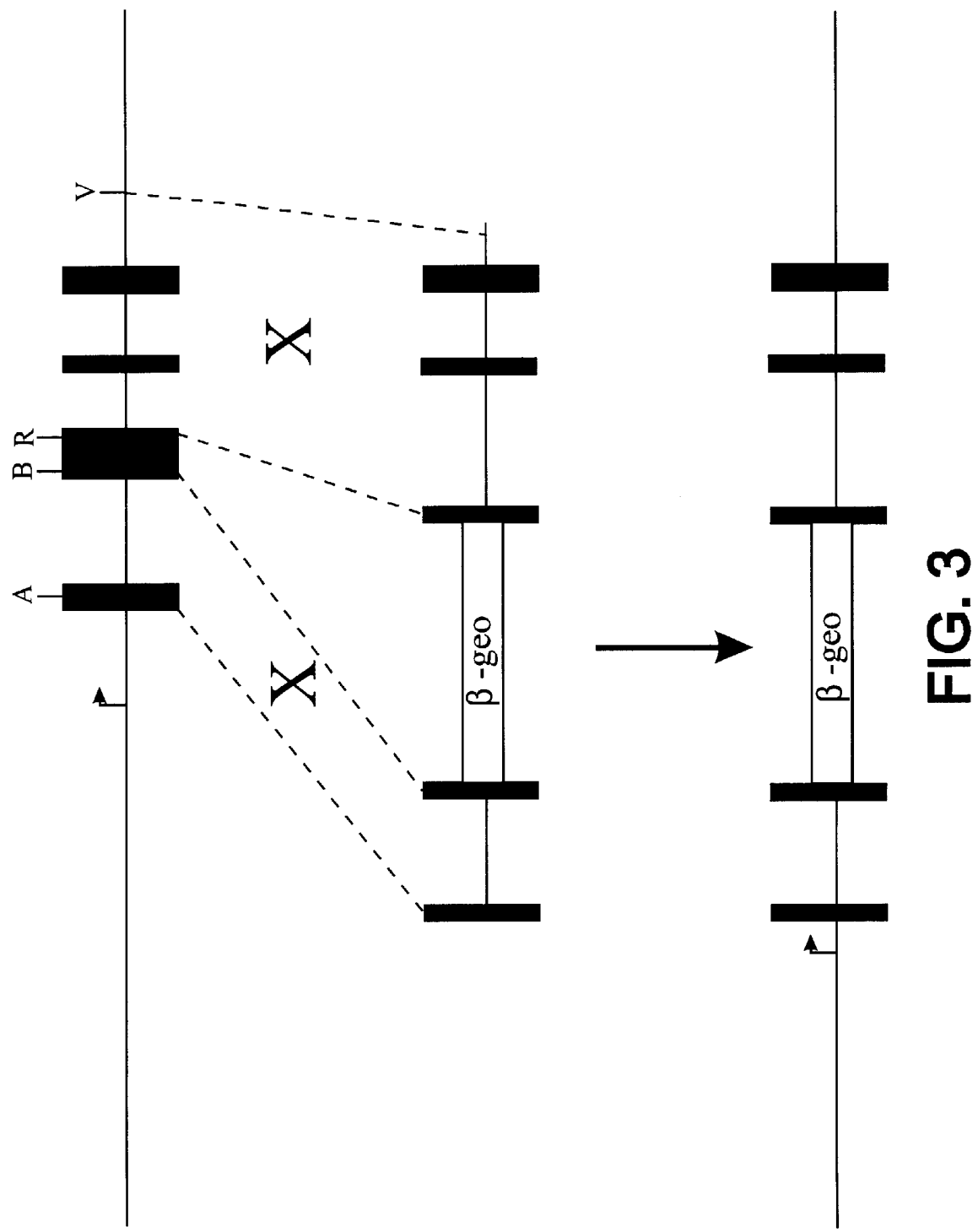
FIG. 3 illustrates the insertional inactivation with the promoterless β-geo cassette. In this construct the β-geo cassette is inserted inframe into exon 2 of Ant1. The combined β-galactosidase and neomycin resistance genes are transcribed from the endogenous Ant1 promoter. A=AsIII; B=BstEII; R=EcoRI; and V=Eco RV.

After the Ant1 locus was cloned and characterized, we devised two separate gene-targeting strategies. One strategy consists of inserting a "knock-in" promoterless βgeo cassette into exon 2 of Ant1 (see FIG. 3). The βgeo gene product is a chimeric protein containing both β-galactosidase activity and neomycin resistance. After homologous recombination in ES cells, the targeted allele is expressed (driven from the endogenous Ant1 promoter) as a fusion transcript containing the first third of Ant1 (exon 1 and the 5′ end of exon 2) and βgeo. A major advantage from this approach is that β-galactosidase activity (via X-Gal staining) marks Ant1 expression in situ.

Figure 2:
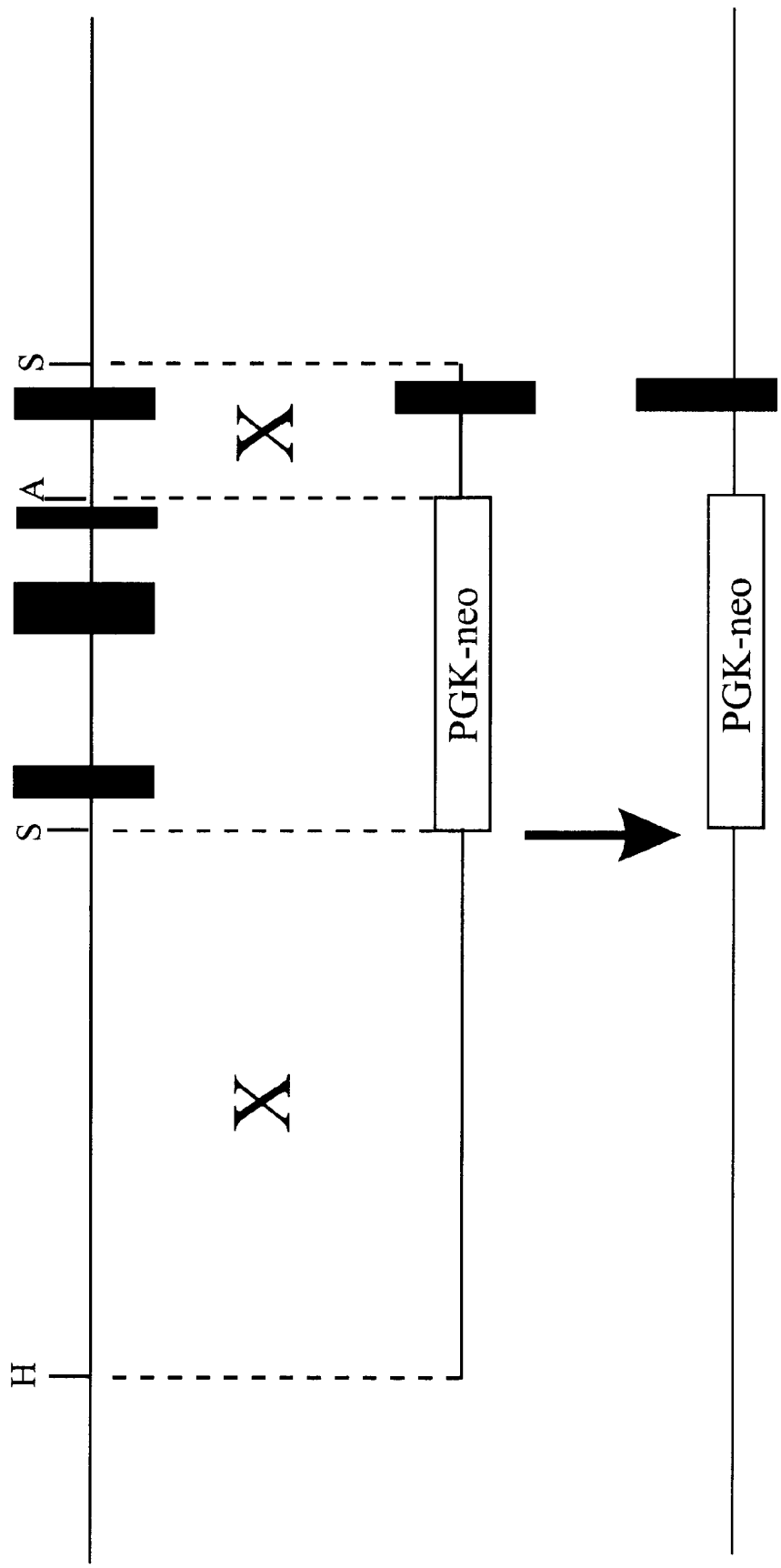
FIG. 2 illustrates the Ant1 deletion with the PGK-neo cassette. The PGK-neo cassette replaces the first three exons of the ANT1 sequences. H=HindIII; A=AsIII; S=SstII.

The second gene-targeting strategy consists of deleting Ant1 locus (exons 1–3) and replacing with PGKneo cassette (see FIG. 2). The PGKneo cassette contains the neomycin resistance gene driven by the phosphoglycerol kinase promoter. This targeted allele is a true null allele.

Using these two gene-targeting constructs, we transfected embryonic stem (ES) cells and selected for neomycin resistance. We then screened the resulting ES cell clones by Southern analysis for homologous recombination events. We were able to isolate multiple ES cell clones in each targeting strategy. Using these ES cell clones for microinjection into donor B6 blastocysts, we generated chimeric mice with both types of targeted alleles. We have established permanent mouse lines to allow phenotypic characterization.

Figure 5:
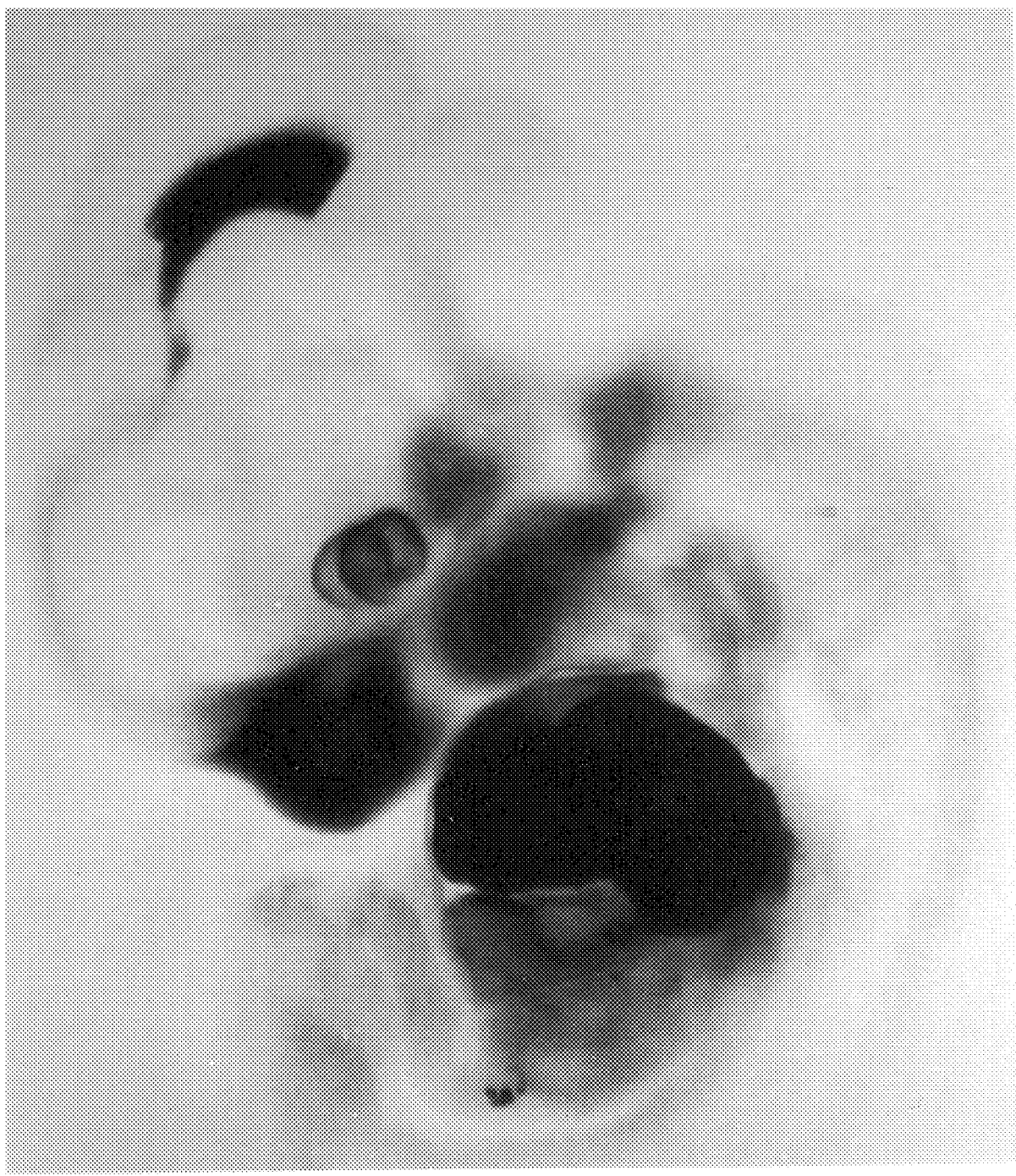
FIG. 5 shows is a color reproduction of an 11.5 day (after conception) embryo which is heterozygous for the β-geo mutant Ant1 gene. The blue-stained areas represent regions where the Ant1 promoter is active. Note, paricularly, the staining of the heart, newly formed somites, and the basal ganglia of the brain.
Figure 6A:
FIG. 6A–6C illustrates the results of β-galactosidase staining of adult tissues of animals heterozygous for the β-geo mutant Ant1 gene.
Figure 6B:
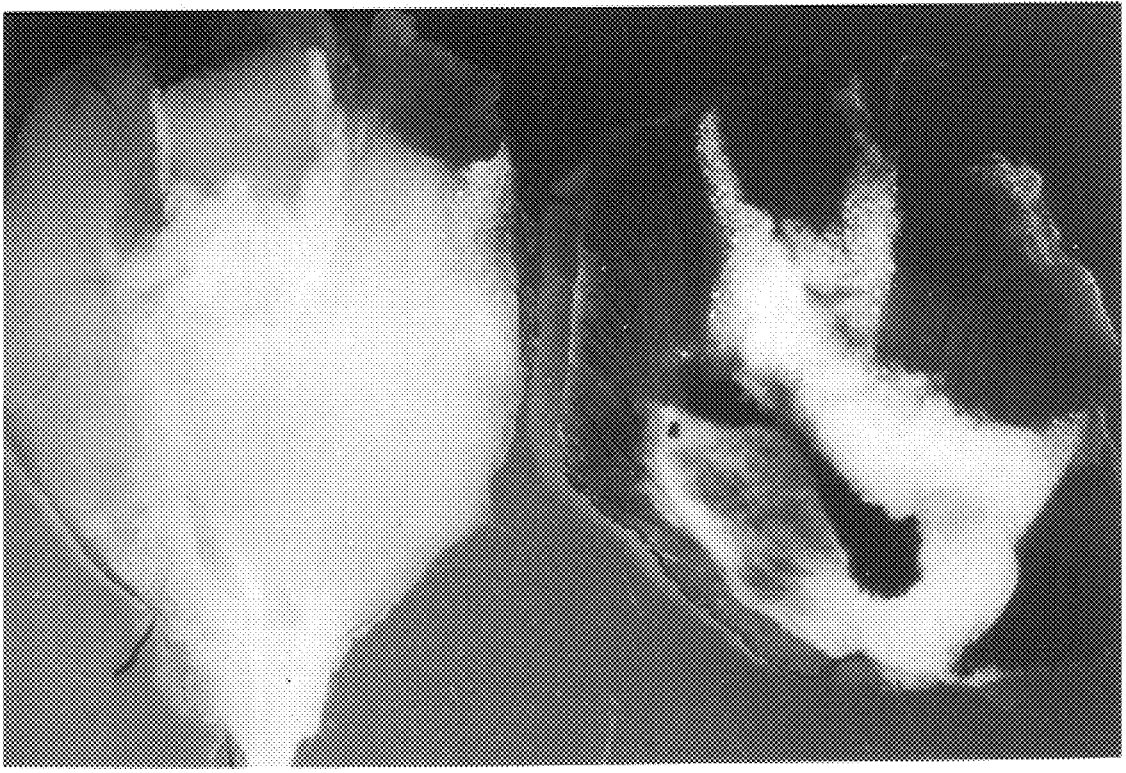
Figure 6C:
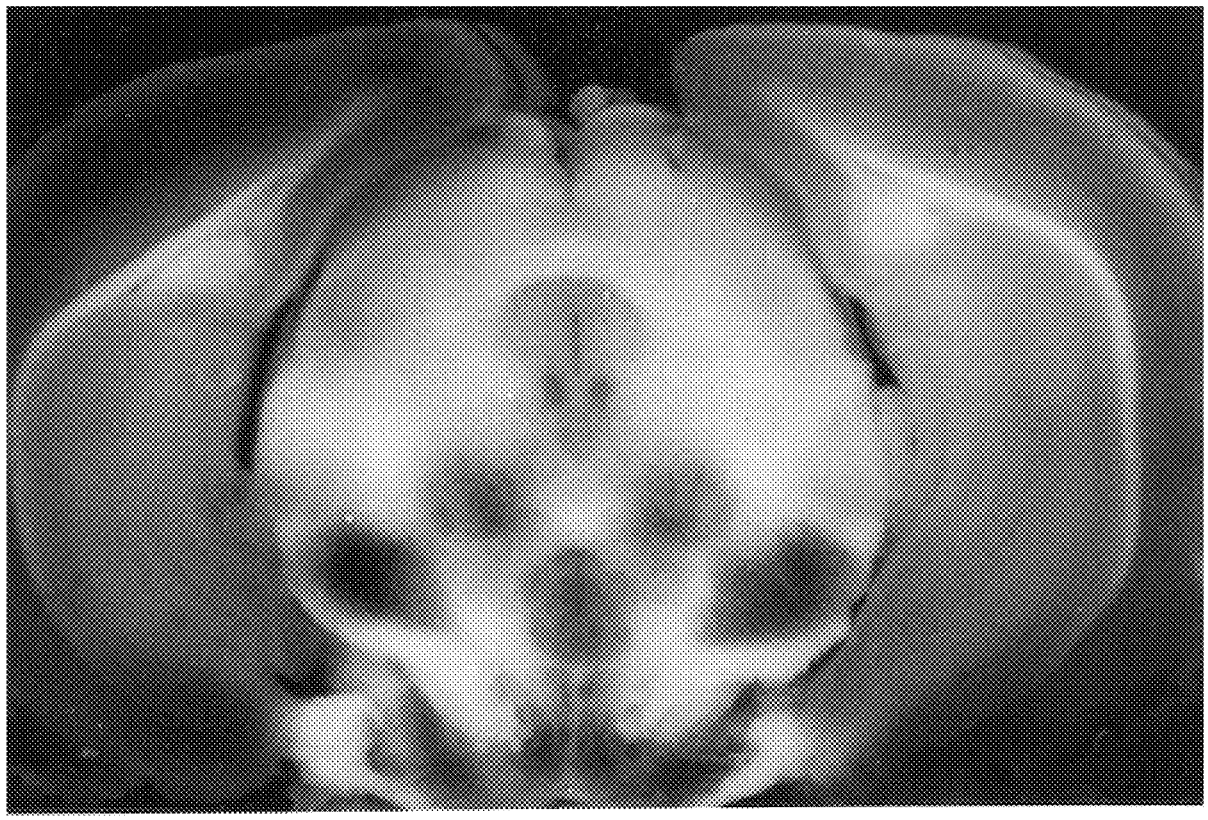

As described hereinbelow, embryos from a cross between an Ant1-βgeo (genotyped using DNA from yolk sac), showed positive X-Gal staining (see FIG. 5). The wild-type siblings exhibited no X-Gal staining. At this embryonic stage, the heart is formed (and is beating), and in this embryo, shows positive X-Gal staining (A in FIG. 5). There is also a distinctive staining pattern in the brain (B in FIG. 5) whose location is consistent with the dopaminergic nuclear complexes of the basal ganglia. In the adult mice examined, cardiac and skeletal muscle showed intense positive X-Gal staining, with the brain exhibiting staining in all major regions, including the cerebral cortex, basal ganglia and cerebellum. See FIGS. 6A, 6B and 6C.

Figure 4:
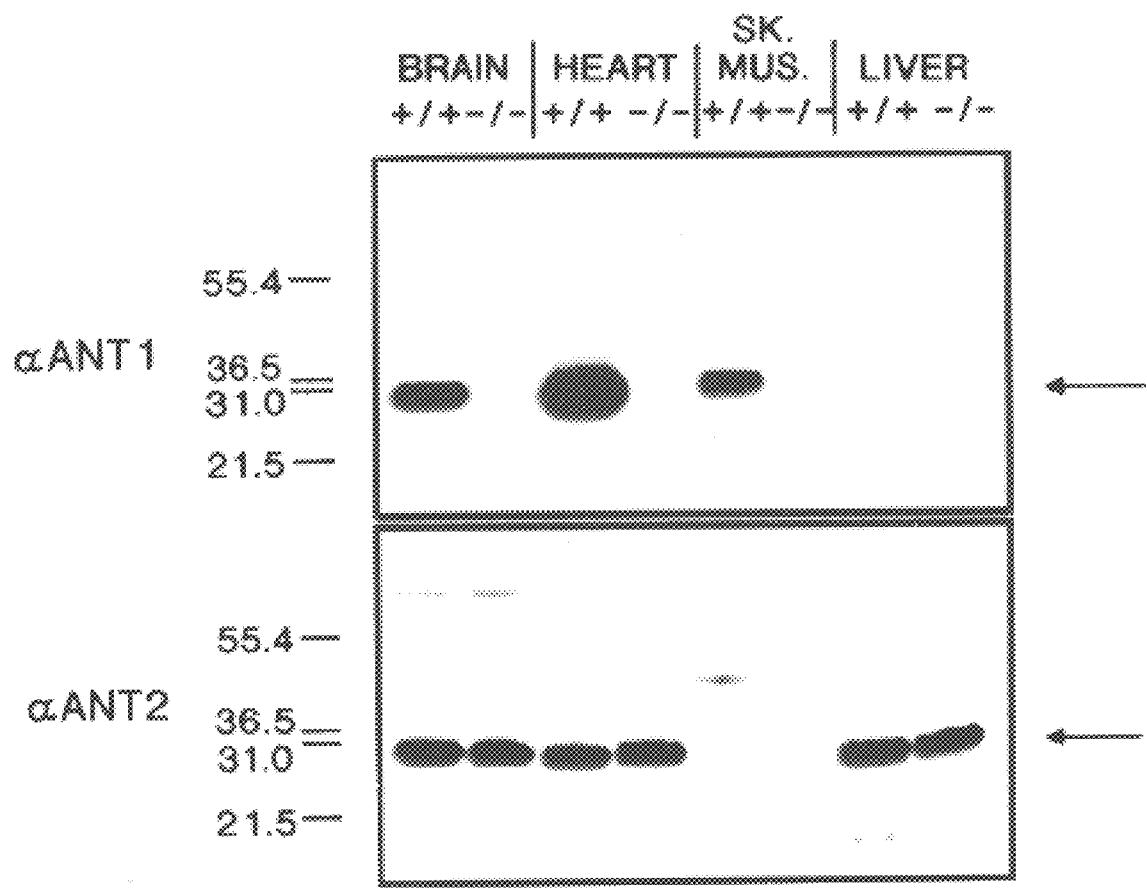
FIG. 4 is a reproduction of Western blot analysis of blot analysis of tissue lysates from wild-type (+/+) and homozygous Ant1$^{PGKneo}$ mice. The antisera are the same as those used for the experiment shown in FIG. 1. The arrows indicate the 30 kDa ANT1 and ANT2 monomers—SK MUS, skeletal muscle (gastrocnemius). The ANT1 protein is not detected in brain, heart and muscle of the (−/−) mice. In kidney, the ANT1 band is reduced in intensity relative to the ANT1 (+/+) mice, but it is not absent.

In addition to the β-geo "knock-in" allele, we created a mutant allele of Ant1 in which exons 1–3 of Ant1 were replaced with a PGKneo cassette that has a strong polyadenylation signal. This mutant allele is null for ANT1 activity. Targeted ES clones were identified and the mutation passed through the germ line as described for the Ant1$^{βgeo}$ mutant allele. Two independent Ant1$^{PGKneo}$ clones underwent germ-line transmission. F1 heterozygotes were generated by the mating of male chimeras with C57BL/6J (B6) females. After a backcross with B6 females, N2 Ant1$^{PGKneo}$ heterozygotes were intercrossed and the progeny genotyped by either Southern blot or PCR analysis. The cumulative genotype ratios (+/+:+/−:−/−) for the offspring were 86:174:90 (0.98:1.99:1.03), which conforms to the expected mendelian ratios (1:2:1). Thus, homozygous Ant1$^{PGKneo}$ mutants are viable. They are also fertile and exhibit normal growth characteristics when compared to their wild-type siblings up to at least eight months of age. Molecular analysis of mutant adult tissue at the level of mRNA (FIG. 13) or protein (FIG. 4) revealed an absence of Ant1 expression. In addition, there was no gross induction of the Ant2 isoform.

Based on tissue-specific expression analysis of Ant1 and Ant2, we focused on skeletal muscle for analysis because it contains the least Ant2 protein (which could compensate for the absence of Ant1 protein) in the mutant mice (see FIG. 7). Histological analysis of mutant frozen muscle sections from 3–4 month old homozygous mutant mice demonstrate ragged-red fibers by Gomori's Trichrome staining as well as increased cytochrome c oxidase and succinate dehydrogenase activities by histochemical staining (see FIGS. 7, 8 and 9). Ragged red fibers are muscle fibers that have a ragged contour and a sarcolemmal accumulation of red-staining material.

Because ragged-red fibers have been associated with proliferation of mitochondria in human mitochondrial myopathies and the observed increased histochemical staining is also consistent with mitochondrial hyperproliferation, we examined skeletal muscle, as well as heart, by electron microscopy (see FIG. 10). Skeletal muscle from an Ant1-PGKneo homozygous mouse exhibits a marked proliferation of mitochondria. Hyperproliferation of mitochondria is also apparent in mutant heart tissue.

In addition to the presence of RRFs, fresh-frozen sections of mutant skeletal muscle exhibited increased succinate dehydrogenase (SDH) and cytochrome c oxidase (COX) activities by histochemical staining. Wild-type sections (FIGS. 8A, 9A) reveal the normal variation in staining intensities, with the larger type II (glycolytic) fibers staining less than the smaller type I fibers. In the mutant muscle, the increased staining is more pronounced in the type I fibers. This increase in OXPHOS histochemical staining is consistent with an accumulation of mitochondria.

To assess any oxidative phosphorylation (OXPHOS) biochemical phenotype, we measured respiration using mitochondria isolated from skeletal muscle, heart, and liver tissue pooled from Ant1 (−/−) and wild-type animals (5 per pool) (see Table 1). Wild-type and mutant liver mitochondria have similar respiration rates, consistent with the observation that Ant1 is not expressed in the liver. However, mutant skeletal muscle mitochondria exhibit a severe reduction in state III (ADP-stimulated) respiration rates relative to controls for both complex I (glutamate+malate or pyruvate+malate) and complex II (succinate) substrates, while maintaining comparable state IV (ADP-limited) rates. In other words, the mutant skeletal muscle mitochondria are insensitive to ADP addition, consistent with impermeability to ATP and ADP. Mutant heart mitochondria show a moderate reduction in state III rates for glutamate+malate, but no significant reduction for the other substrates. These results demonstrate that a tissue-specific block in ATP production causes mitochondrial proliferation and RRFs in the tissue in which ATP is depleted.

Ant1-deficient heart mitochondria exhibited a 34% reduction in state III respiration rates when compared to wild-type mitochondria for the complex I substrates glutamate+malate, but did not show a difference when other substrates were used. By contrast, the state III and state IV respiration rates of mutant mouse liver mitochondria were indistinguishable from those of controls. This indicates that loss of Ant1 expression had no effect on ADP and ATP permeability in liver mitochondria, consistent with the predominance of Ant2 expression in liver.

To further characterize the muscle mitochondria of Ant1$^{PGKneo}$ homozygous animals, we examined the cellular ultrastructure of both mutant and control skeletal muscle. Analysis of mutant skeletal muscle revealed a marked proliferation of mitochondria compared to wild-type skeletal muscle. This proliferation is greatest in the subsarcolemmal region, especially near vasculature, but accumulations of mitochondria are also present in the intermyofibrillar regions. In the intermyofibrillar regions, the myofibrils appeared to be displaced, indented or even completely overwhelmed by the sheer abundance of mitochondria. Many of the mitochondria present in the mutant skeletal muscle are much larger than mitochondria in wild-type skeletal muscle. This type of skeletal muscle ultrastructural pathology is a hallmark of mitochondrial myopathy [DiMauro et al. (1985) Ann.Neurol. 17:521–538].

Examination of 4–6 month-old mice revealed that the hearts from mutant individuals appeared grossly enlarged compared to those from age-matched controls. This observations was substantiated by comparison of the wet weight (normalized to body weight) of hearts in both mutants and age-matched controls. Ant1-deficient mice (n=5) had a mean heart wet weight of 7.23±0.77 mg/g body weight (P=0.0011 by two-tailed, unpaired t-test) The normal heart weights are comparable with those in published morphometric studies [Barth et al. (1992) J. Mol. Cell. Cardiol. 24:669–681]. No difference in heart size was apparent between younger (6–8 week-old) mutant and control mice. Histological analysis confirmed the presence of cardiac hypertrophy, as evidenced by a thickening of the walls of the left ventricle.

Examination of mutant heart muscle ultrastructure also revealed an increase in mitochondria when compared to wild-type heart. Interestingly, there did not appear to be any significant increase in size or change in appearance of mutant heart mitochondria relative to normal heart mitochondria, in contrast to the situation for skeletal muscle.

To determine whether the severe OXPHOS defect in homozygous mutant skeletal muscle resulted in metabolic abnormalities, we collected and pooled blood from both wild-type (n=5) and mutant (n=5) mice and measured the plasma organic and amino acid levels Table 2). The Ant1-deficient mice exhibited a fourfold higher resting serum lactate level than age- and gender-matched controls, while maintaining similar pyruvate levels. The wildtype resting serum lactate level was comparable to previously published values for normal mice [Hatchell and MacInnes (1973) Genetics 75:191–198]. The Krebs cycle intermediates succinic acid and citric acid were elevated 48-fold and 1.7-fold, respectively, in the mutant mice as well. Alanine was also elevated in plasma, with mutant mice having 50% higher levels than controls (Table 3). Therefore, mice lacking Ant1 exhibit a metabolic profile consistent with OXPHOS deficiency.

A common characteristic of human patients with OXPHOS-deficient mitochondrial myopathy is a reduced tolerance for exercise and a lowered anaerobic threshold [Wallace et al. (1988) Cell 55:601–610]. We therefore subjected the Ant1$^{PGKeno}$ mutant mice to an incremental exercise stress test (see FIGS. 14A–14B). Six normal (three wild-types and three heterozygotes) and six homozygous animals were exposed to a 25-min exercise protocol comprising incremental increases in speed and inclination of a treadmill belt. All normal individuals were easily able to complete the exercise protocol, even at the highest speeds and inclinations employed. By contrast, none of the mutants were able to complete the protocol, and they collapsed from fatigue. On average, the homozygous mutant animals were able to complete only 54% (+22%) of the protocol. Moreover, there was a consistent gender difference between mutant animals, with mutant males showing a twofold greater capacity to endure the exercise test than mutant females: 75%±1% (n=3) for males versus 35%+5% (n=3) for females (FIG. 14A). Without wishing to be bound by theory, this gender difference is believed to reflect the greater muscle mass present in males, which could provide increased resistance to fatigue. Nevertheless, since neither the normal male nor the normal female mice showed any evidence of fatigue in the current exercise regimen, it is clear that the mutant mice, both male and female, are far more exercise intolerant than normal mice.

Measurement of rates of oxygen consumption ($V_{O_2}$) and carbon dioxide production ($V_{CO_2}$) during the exercise stress test also revealed a striking difference between normal and mutant mice. The normal mice exhibited a directly proportional relationship between the rates of $V_{O_2}$ and $V_{CO_2}$, which remained constant during the entire test. This relationship is summarized by the respiratory exchange ration (RER), which is the ratio of $V_{CO_2}$ to $V_{O_2}$. The mutant mice, by contrast, exhibited an increasing RER with increasing levels of work before exhaustion and collapse. This change in the RER with increasing work was primarily the product of a decline in $V_{O_2}$ (FIG. 14B).

In this study, we generated mice that were deficient for Ant1. These animals exhibited the classical anatomical, histological, biochemical, metabolic and physiological features associated with mitochondrial myopathy and cardiomyopathy. Their development of myopathy and hypertrophic cardiomyopathy provides the first cause-and-effect demonstration that a defect in mitochondrial energy metabolism can result in heart and muscle disease.

Histologically, the RRFs observed in these mutant mice are strikingly similar to those seen in human mitochondrial myopathy and are the first to be observed in mice. In human mitochondrial myopathies, the RRF phenotype has been correlated ultrastructurally with the proliferation of enlarged, abnormal mitochondria, and this is precisely what was observed in the Ant1 (−/−)mutant mice.

Mouse skeletal muscle mitochondria lacking ANT1 exhibit a severe defect in ADP-stimulated respiration. This defect is consistent with an absence of ADP/ATP transport across the inner mitochondrial membrane. This proves that ANT1 is by far the predominant, if not the only, mitochondrial inner membrane protein capable of ADP/ATP exchange. It also provides a direct genetic test for the stringent coupling between the electron transport chain and the ATP synthase. The predicted metabolic consequence of this defect is a reduction in electron transport and a resulting accumulation of NADH, increasing the [NADH+H$^+$]/[NAD$^+$] ratio. These changes inhibit the Krebs cycle, causing an accumulation of pyruvate and other Krebs cycle intermediates. The excess NADH then promotes the reduction of the pyruvate to lactate to regenerate oxidized NAD$^+$ for glycolysis. The accumulated pyruvate would also interact with transaminases to yield alanine. Thus, the Ant1 -deficient mice exhibit the metabolic profile of resting lactic acidosis, increased lactate/pyruvate ratio, increased Krebs cycle intermediates and increased alanine levels. This profile conforms qualitatively and quantitatively to the general metabolic profile of human patients with mitochondrial myopathy due to respiratory chain defects [Munnich et al. (1996) *Eur. J. Pediatr.* 155:262–274].

In addition to mitochondrial myopathy, Ant1 -deficient mice exhibited progressive cardiac hypertrophy associated with mitochondrial proliferation. A similar concentric hypertrophy is observed in human patients with mitochondrial cardiomyopathy caused by respiratory chain deficiencies [Servidei et al. (1994) *Adv. Pediatr.* 41:1–32]. In contrast to mutant skeletal muscle mitochondria, mutant heart mitochondria demonstrated only an apparent partial defect in coupled respiration. This difference is believed to be due to the limited expression of Ant2 in the heart mitochondria, which provides some ADP/ATP transport and prevents neonatal bioenergetic failure and death.

The physiological manifestations of the OXPHOS deficiency induced by Ant1 deficiency in these mice are associated with a severe exercise intolerance. In human patients with severe mitochondrial myopathy, as is found in the syndrome of mitochondrial encephalopathy with ragged-red fibers (MERRF), there is exercise intolerance associated with a reduced anaerobic threshold. The reduced anaerobic threshold results from the reduced OXPHOS capacity and increased lactate production in these patients. The incremental exercise stress testd employed herein subjected the normal mice to workloads far below their maximum aerobic capacity, as evidenced by their constant RER under increasing levels of work. For the mutant mice, however, the same test resulted in fatigue and ultimately collapse associated with an increasing RER. This observation cannot be due solely to a decreased anaerobic threshold because an increasing RER above the anaerobic threshold is related to increasing $V_{CO_2}$ (reflecting buffering of increased plasma lactate by bicarbonate) rather than decreasing $V_{O_2}$. Thus, while it seems likely that the Ant1$^{PGKeno}$ mutants have a reduced anaerobic threshold, given their resting lactic acidosis, the rapid fall in $V_{O_2}$ also reflects cadiovascular dysfunction induced by stress. Hypertrophic cardiomyopathy is observed in the Ant1 (−/−) mice by about 6 months of age.

Central nervous system involvement in mitochondrial diseases is frequently observed. Even though Ant1 is expressed in mouse brain, no gross neurologic abnormalities have yet been observed in the Ant1$^{PGKeno}$ mice (for example, abnormal behavior, abnormal posturing or gait, seizures), at least up to about eight months of age. Without wishing to be bound by theory, this is believed to reflect the co-expression of Ant1 and Ant2 in the brain.

There is one case report of a patient with mitochondrial myopathy and lactic acidosis due to a deficiency of ANT in skeletal muscle [Bakker et al. (1993) *Pediatr. Res.* 33:412–417]. This patient's condition clinically improved upon treatment with vitamin E [Bakker et al. (1993) *J. Inherit. Metab. Dis.* 16:548–552]. Despite the demonstration by immunoblot analysis of a decrease of muscle ANT in this patient, no genetic defect in any human ANT gene has been reported. Nevertheless, on the basis of the phenotype of the Ant1$^{PGKneo}$ mouse, there is a subset of patients with mitochondrial myopathy and/or cardiomyopathy resulting from mutations affecting the expression or activity of ANT1. One such disease is fascioscapularhumeral muscular dystrophy. This disease manifests progressive muscle degeneration and cardia problems and maps to chromosome 4q, in close proximity to the human ANT1 homologue [Wijmenga et al. (1993) *Human Genetics* 92:198–203; Haraguichi et al. (1993) *Genomics* 16:479–485]. Hence, the present Ant1 (−/−) mouse provides a useful model system in which to test compounds for therapy for mitochondrial disease, especially that resulting from Ant1 deficiency.

Thus, we have successfully targeted the Ant1 locus for inactivation and have generated mice lacking the Ant1 protein. Preliminary analysis of ant1 expression in situ using X-Gal staining in Ant1-βgeo heterozygotes shows expression in heart and skeletal muscle as well as a distinctive brain expression pattern. Initial characterization of mutants reveals that homozygotes are viable at least until young adulthood, but they also exhibit ragged-red fibers in skeletal muscle, prolification of mitochondria in skeletal muscle and heart, defective coupled respiration in skeletal muscle, and an elevated resting blood lactate level. Thus, mice lacking Ant1 expression manifest biochemical histological, ultrastructural, and metabolic characteristics of a mitochondrial myopathy. (Shoffner and Wallace in *The Metabolic and Molecular Bases of Inherited Disease*, McGraw-Hill, Seventh Edition, 1994).

The ANT1-deficient mice of the present invention are useful models of mitochondrial disorders of humans, and other animals, especially mammals. The mice of the present invention provide a useful animal model in which to test gene therapies and pharmaceutical compositions for efficacy in mitochondrial diseases due to defects in oxidative phosphorylation, especially those resulting from defects in nuclear genes.

The present work proves that OXPHOS defects cause mitochondrial disease, and the present Ant1 (−/−) transgenic mouse provides the first mitochondrial disease animal model. It follows that knocking out tissue-specific isoforms of other nuclear encoded OXPHOS genes (for example, the cytochrome oxidase tissue-specific isoforms for subunits VIa, VIIa, and VIII [Kadenback and Merle, (1981) *FEBS. Let.* 135:1–11; Lomax and Grossman, (1989) *TIBS* 14:501–503] could provide additional animal models for mitochondrial diseases affecting these and other tissues. Such models are then useful to analyze the pathophysiology of mitochondrial disease and for developing new metabolic and genetic therapies.

Monoclonal or polyclonal antibodies, preferably monoclonal, specifically reacting with an ANT1 or ANT2 protein may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Ausubel et al. (1993) *Current Protocols in Molecular Biology*, Greene Pub. Ass. Inc. & John Wiley & Sons, Inc., Boston, MA; Sambrook et al. (1989) *Molecular Cloning*, Second Edition, Cold Spring Harbor Laboratory, Plainview, New York; Maniatis et al. (1982) *Molecular Cloning*, Cold Spring Harbor Laboratory, Plainview, New York; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, New York; Old and Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

All references and patent publications cited in the present application are incorporated by reference herein.

The following examples are provided for illustrative purposes, and is not intended to limit the scope of the invention as claimed herein. Any variations in the exemplified methods which occur to the skilled artisan are intended to fall within the scope of the present invention.

EXAMPLES

Example 1

Animal Model

Mice lacking functional ANT1 were produced using two different strategies. In the first, the first three (of four) exons of Ant1 were deleted and replaced with a neomycin resistance gene (neo) expressed under the control of a phosphoglucokinase (PGK) promoter (see FIG. 2). In the second strategy, the second exon of Ant1 was modified to incorporate an in-frame fusion of "βgeo", which contains both the neo and the β-galactosidase coding sequence expressed under the control of the Ant1 promoter (see FIG. 3). Both constructs impart resistance to G418, therefore, recombinant cells can be selected using G418 in the culture medium.

The Ant1$^{\beta geo}$ targeting vector was constructed in two steps. First, a 1.5-kb Ant1 genomic fragment encompassed by the AflII site (blunted end) in exon 1 and the first BglII site (blunted end) in exon 2 was cloned into a BamHI site (blunted end) immediately 5' of the β-geo coding sequences in pBSβ-geobpA [MacGregor et al. (1995) *Development* 121:1487–1496]. The inframe fusion between exon 2 of Ant1 and β-geo was confirmed by DNA sequencing. Second, a 3.6-kb Ant1 and genomic fragment encompassed by the EcoRI site in exon 2 and the EcoRV site approximately 1.3-kb 3' of exon 4 was cloned 3' of the β-geopbA sequence. The total length of homology was 5.1 kb. Northern analysis of 129/Sv ES cell RNA with a human ANT1 cDNA probe revealed that Ant1 is expressed in ES cells.

The Ant1$^{PGKneo}$ targeting vector was also constructed in two steps. First, a 5.4-kb HindIII-SstI Ant1 genomic fragment, immediately 5' of the Ant1 coding region, was cloned 5' of the PGKneo cassette in pPGKneopbA [Soriano et al. (1991) *Cell* 64:693–702]. Second, a 1.2-kb Ant1 genomic fragment encompassed by the AflII site in intron 3 and the SstI site 3' of exon was cloned 3' of the PGKneobpA sequence. The total length of homology was 6.6 kb.

For each targeting vector, 25 μg of DNA, separated from vector sequences by digestion at unique restriction sites flanking the gene-targeting sequences, was introduced into AK7.1 129/Sv ES cells by electroporation [Ramirez-Solis et al. (1995) in Guide to Techniques in Mouse Development, Vol. 225 (eds. Wasserman, P. M. and DePamphlis, M. L.), pp. 855–878, Academic Press, San Diego, Calif.]. Neomycin-resistant clones were selected with G418 (GIBCO, 300 μg/ml), and properly targeted homologous recombinants (2/6 for Ant1$^{\beta\text{-geo}}$, 3/168 for Ant1$^{PGKneo}$) were identified by Southern analysis using 5' and 3' genomic DNA probes, from regions external to the homologous arms of the targeting vectors, as well as an internal neo probe. Correctly targeted clones were injected into C57BL/6J blastocysts, and the resulting male chimaeras were bred with C57BL/6J females for targeted allele transmission. All ES culture, Southern blot, microinjection and animal husbandry techniques were performed as described [Ramirez-Solis et al. (1993) supra; Stewart, C. L. (1993) in Guide to Techniques in Mouse Development, Vol. 225 (eds. Wasserman, P. M. and DePamphlis M. L.) pp. 823–855, Academic Press, San Diego, Calif.].

The genotypes of 6–9 day old pups is determined by genetic analysis of tissue surgically excised from the toe or tail tip (2–3 mm). In the mice with PGKneo insertion the first three exons of the Ant1 gene have been deleted, thus, destroying the ability to synthesize an active ANT1 protein. In mice having the ANT1 gene disrupted by the inframe insertion of the βgeo cassette, exon 2 is disrupted.

Genetic analysis of tissue is done by first extracting DNA from each tissue sample using Proteinase K digestion (12 min) at 55° C. in 50 μl of 1×PCR buffer (10 mM Tris-HCl, pH 8.3, 50 mM KCl, 1.5 mM $MgCl_2$), 0.5 mg/ml proteinase K, 0.05% Nonidet P-40 (NP-40), and 0.05% Tween-20. After proteinase K inactivation (15 min. at 95° C.), 1 μl was then used in a 50-μl multiplex polymerase chain reaction using three primers for Ant1-PGKneo genotyping:

MANTIE3K,
5'-ATGATGATGCAGTCTGCCCGGAAA-3' (SEQ ID NO:3);

MANTIE4T, 5'-GATCTCATCATACAATACCAATACA-3' (SEQ ID NO:4); and

PGKneo-f, 5'-AGGATTGGGAAGACAATAGCAGGC-3' (SEQ ID NO:5); and three primers for ANT1-βgeo genotyping:

MANTIE2G,
5'-GCCAGCAAACAGATCAAGTGCAGAG-3' (SEQ ID NO:6);

MANTIE2R,
5'-TGAAGATCTTGGTGAGACAGTCGCC-3' (SEQ ID NO:7); and

2629(βGEO),
5'-CCGTGCATCTGCCAGTTTGAGGGGA-3' (SEQ ID NO:8).

Reaction conditions were as follows: hot start (94° C.) followed by 35 cycles of 96° C., 10 sec; 65° C., 30 sec; 72° C., 45 sec in a reaction volume of 50 μliters containing DNA (20 to 100 ng), 20 mM Tris, pH 8.9, 10 mM KCl, 10 mM $(NH_4)_2SO_4$, 2 mM $MgSO_4$, 0.1% Triton S-100, 0.1 mg/ml nuclease-free acetylated bovine serum albumin, 200 μM dNTPs, 300 nM each of the three primers, and 0.05 units/μliter Taq DNA polymerase. Amplification products were then analyzed by agarose gel electrophoresis: ten microlitres of each reaction was then electrophoresed on a 2% agarose gel (3:1 high resolution blend, AMRESCO) and visualized by ethidium bromide staining. Genotype analysis by PCR using the PGKneo primers results in the production of 994 bp and 880 bp amplimers for the wild-type and Ant1-PGKneo alleles, respectively. Where the βgeo primers are used for PCR genotyping, amplimers of 375 bp and 450 bp are produced for the wild-type and Ant1-βgeo alleles, respectively. The homozygous Ant1 (−/−) mouse DNA produces only the 880 or 450 bp amplification product, the wild-type mouse DNA produces only the 994 or 375 base product, while the heterozygote produces amplimers of both sizes due to the presence of both forms of the gene. The skilled artisan understands that alternative primers can be designed and amplification products can be expected for these mice or where a different disruption of the ANT1 gene is used. Absence of the ANT1 protein is confirmed by Western analysis on tissue lysates in which the proteins have been size-separated by polyacrylamide gel electrophoresis.

Example 2

Animal Husbandry

Mice are housed under standard animal housing conditions with a normal day/night cycle and fed normal mouse chow (not high-fat). Nursing mothers are housed in individual cages with their offspring. They have free access to food and water (ad libitum). Fresh bedding and a change of cage litter is provided twice per week.

Test mice are weighed daily to allow calculation of appropriate dosage of test compounds, but otherwise, handling is kept to a minimum to reduce stress on nursing mothers.

Example 3

Methods

The mouse Ant1 locus was cloned from a 129/Sv genomic library (λDASHII) using human Ant1 cDNA [Necklemann et al. (1987) Proc. Natl. Acad. Sci. USA 84:7580–7584] as a probe. One positive clone was isolated from $1 \times 10^6$ plaques screened. The insert of this genomic clone was 15 kb long, and the entire Ant1 gene was localized to a 4.5-kb SstI DNA fragment, which was subcloned along with adjacent genomic segments into separate pBluescript vectors (Stratagene, LaJolla, Calif.) for further characterization. To facilitate gene targeting, the genomic subclones were mapped with several restriction enzymes, and exons 1–4 of Ant1 were localized to specific fragments with exon-specific oligonucleotide hybridization. The exon-specific oligonucleotide sequences were derived from the Ant1 cDNA sequence (see below, SEQ ID NOs:9 and 11), and exon boundaries were predicted by comparison to the human ANT1 genomic sequence [Li et al. (1989) J. Biol. Chem. 264:13998–14004.]

In SEQ ID NO:9, the coding sequence of exon 1 corresponds to nucleotides 94–204, exon 2 corresponds to nucleotides 205–691, exon 3 corresponds to nucleotides 692–832, and exon 4 begins at nucleotide 693; the coding sequence ends at nucleotide 990.

SEQ ID NO:10 (in IUPAC code) is the cDNA sequence determined for the mouse Ant1 by the present inventors, and SEQ ID No:11 is the deduced amino acid sequence for the encoded protein.

Ant1 and Ant2 cDNAs were cloned by screening of a mouse heart cDNA library (λZAPII, Stratagene) with human ANT1 and ANT2 cDNAs [Necklemann et al. (1987) supra; Battini et al. (1987) J. Biol. Chem. 262:4355–4359] as probes. The cDNA sequences were determined by DNA Taq dyedeoxy terminator cycle sequencing (ABI) and are in agreement with recently published sequences [Ellison et al. (1996) Mamm. Genome 7:25–30]. Because of the inability to isolate a mouse ANT3 homologue, the previous report of detection of a mouse Ant3 mRNA through cross-hybridization with a human ANT3 cDNA [Stepien et al. (1992) J. Biol. Chem. 267:14592–14597] is believed to be due to cross-hybridization between the ANT3 cDNA and mouse ant1 mRNA.

To make transgenic mice in which the Ant1 locus is inactivated, two strategies were pursued. See FIGS. 2 and 3 for details. The vectors carrying these constructs were introduced into embryonic stem cells (ES), gene-targeting and blastocyst injections were carried out essentially as previously described [Hogan et al. (1994) Manipulating the Mouse Embryo, Cold Spring Harbor Laboratory Press, Cold Spring Harbor, N.Y.]. Mice were genotyped as described hereinabove.

For Northern hybridization, total RNA was extracted from dissected adult mouse tissues using single-step acid guanidium thiocyanate-phenol-chloroform extraction (RNA STAT-60, TEL-TEST "B", INC.). RNA (5 μg RNA/lane) was denatured with glyoxal, electrophoresed on a 1.2% agarose gel, blotted to Hybond-N nylon (Amersham), and probed with mouse Ant1 and Ant2 cDNAs (cDNAs were cloned from a mouse heart cDNA library using human Ant1 and Ant1 cDNAs as probes) and Mouse 18S rDNA as a loading control.

For Southern hybridization of wild-type and Ant1-PGKneo mice, genomic DNA was isolated from the spleens of Ant1-PGKneo mice, fully digested with EcoR1, electrophoresed on a 0.85% agarose gel, blotted to Hybond-N+ nylon (Amersham) under alkaline conditions, and probed with 5' and 3' probes (see FIG. 13).

For β-galactosidase activity staining of tissues from wild-type and Ant1-βgeo mice, Ant1-βgeo male chimera was mated with a B6 female, and embryos were harvested at gestational day 11.5. The embryos and/or dissected adult tissues (from a heterozygous Ant1-βneo female) were fixed for 1 hour in 4% paraformaldehyde (100 mM $NaPO_4$, pH 7.4), 0.02% NP-40, 0.01% sodium deoxycholate, rinsed four times in PBS, and stained overnight at 37° C. in X-Gal stain (1 mg/ml X-Gal, 100 mM $NaPO_4$ pH 7.4, 3 mM ferrocyanide, 3 mM ferricyanide, 1.3 mM $MgCl_2$, 0.02% NP-40, 0.01% sodium deoxycholate) [MacGregor et al. (1995) Development 121:1487–1496]. X-Gal is 5-bromo-4-chloro-3-indolyl-β-D-galactopyranoside. Embryos were serially dehydrated in ethanol, cleared in methyl salicylate (oil of wintergreen) and photographed.

For histochemical analysis, the gastrocnemius muscle was dissected and promptly frozen in isopentane supercooled by liquid nitrogen. 10 μm thick frozen transverse sections were cut on a Leica cryostat and stained with modified Gomori's Trichrome, as well as for cytochrome c oxidase (COX) and succinate dehydrogenase (SDH) activities [Sheehan and Hrapschak (1980) *Theory and Practice of Histotechnology*. Batelle Press, 2nd Edition; Rifai, Z., et al. (1995) *Ann. Neurol.* 37:24–29; Dubowitz, V. (1985) Muscle Biopsy, A Practical Approach, Lavenham Press]. The COX histochemical stain contains DAB (3,3'-diaminobenzidine tetrahydrochloride), which gives a brown product with COX activity. The SDH histochemical stain contains NBT (nitroblue tetrazolium), which gives a blue product with SDH activity.

Dissected hearts were washed briefly in PBS to remove as much blood as possible, then were fixed in 10% neutral buffered formalin, embedded in paraffin blocks, sectioned (7–10 μm) transversely and stained with haematoxylin and eosin [Sheehan and Hrapschak (1980) supra]. All photomicrographs were taken on a Zeiss Axiophot microscope.

For electron microscopy analysis, the gastrocnemius muscle and the heart were dissected and cut into 0.5 mm cubes, fixed for one hour (room temperature) in 1% glutaraldehyde (in PBS), washed in PBS (room temperature), and processed for staining, embedding and sectioning as previously described [Blau and Compans (1995) *Virology*. 210:91–99]. Specimens were then examined and photographed using a Philips CM10 electron microscope.

For studies of respiration, for both wild-type and Ant1 mutant, tissues (skeletal muscle, heart, and liver) from wild-type and mutant mice, were pooled separately from 5 adult (5 months old) males, and mitochondria were isolated as previously described [Trounce et al. (1996) *Methods in Enzymology*. 264:484–509]. Material was kept on ice throughout the entire procedure. The pooling of tissues was necessary to achieve a sufficient yield of mitochondria from heart for respiration measurements. Tissues were minced with scalpels, homogenized (10% w/v) in isolation buffer (210 mM mannitol, 70 mM sucrose, 1 mM EGTA, 5 mg/ml BSA [fatty acid free, serum fraction V], and 5 mM HEPES, pH 7.2) with a ground-glass tissue homogenizer (KONTES). Mitochondria were isolated by differential centrifugation [Trounce et al. (1996) supra].

Respiration rates were measured in terms of oxygen consumption over time with a Clark electrode in an enclosed metabolic chamber as described by Trounce et al (1996) supra.

Mitochondrial protein concentrations were estimated by the method of Lowry [Lowry et al. (1951) *J. Biol. Chem.* 193:265–275] and corrected for the BSA content in the buffer.

Whole blood from 5-month-old male wild-type and mutant mice was collected by cardiac puncture of anaesthetized animals and placed in ice-cold heparin-coated tubes. Blood was pooled for both normal (n=5) and mutant (n=5) mice, and the organic and amino acid levels were measured by the Emory Genetics Laboratory.

In exercise stress testing, all experiments using animals were conducted with protocols approved by the Emory University Institutional Animal Care and Use Committee. Each animal was exercised on an enclosed treadmill (Columbus Instruments, Columbus, Ohio) supplied with an electrified grid at the rear of the belt to provide motivation. After an initial 5-min baseline, the mice were subjected to a 20-min exercise protocol, under constant supervision, during which the workload was increased every 2 min by increase of the belt speed and/or the belt incline. The protocol was thus composed of the following: 0–5 min (at rest), 5–7 min (5 m/min, 0° incline), 7–9 min (7 m/min, 0° incline), 9–11 min (10 m/min, 0° incline), 11–13 min (12 m/min, 0° incline), 13–15 min (15 m/min, 0° incline), 15–17 min (15 m/min, 5° incline), 17–19 min (15 m/min, 10° incline), 19–21 min (15 m/min, 15° incline), 21–23 min (15 m/min, 20° incline), and 23–25 min (15 m/min, 25° incline). Each animal was subjected to a 10-min run (belt speed=5 m/min, 0° incline) the day before actual experiments to allow it to become acclimated to the system. Gas measurements were made during the exercise protocol using an open-flow respirometry system (OXYMAX, Columbus Instruments). Data were collected by computer using the OXYMAX software (v. 5.00). The measurement window was set to 30 second intervals. Each animal was subjected to the protocol at least twice on separate days. Fatigue was defined as occurring when an animal could not maintain the pace of the treadmill belt and fell back onto the electrified grid for at least 10 seconds. At this point, the animals were removed and allowed to recover.

Western blots were prepared using polyclonal antibodies raised against ANT1 and ANT2 oligopeptides (15 mers) derived from their respective N-terminal sequences. Unlike most nuclear encoded proteins in the mitochondria, ANT does not have an N-terminal targeting sequence and thus is not processed at the N-terminus upon import into the mitochondrion [Pfanner and Neupert (1987) *J. Biol. Chem.* 262:7528–7536].

The ANT1 and ANT2 amino acid sequences were predicted from their respective cDNA sequences, with ANT1 and ANT2 showing 98% amino acid identity with human ANT2. The ANT1 oligopeptide antigen (SEQ ID NO:1) used was MGDQALSFLKDFLAG(C) and the ANT2 oligopeptide antigen used was MTDAAVSFAKDFLAG(C) (SEQ ID NO:2). (C) denotes a foreign cysteine residue added to the C-terminus to facilitate coupling to BSA. The synthetic oligopeptides were synthesized by the Emory University Michrochemical Facility, coupled to BSA, and used to immunize NSW Rabbits (HRP, Denver, Pa.). Antisera were purified by affinity chromatography first on BSA-Agarose (Sigma, St. Louis, Mo.) and then on their respective peptide-Sepharose columns: ANT1 (MGDQALSFL(C)) (amino acids 1–9 of SEQ ID NO:1) (QCB Inc., Hopkinton, Mass.) and ANT2 (MTDAAVSFAKDFLAG(C)) (SEQ ID NO:2). Tissues for western blot analysis were dissected and lysed (1:3 w/v) in an isotonic buffer (210 mM mannitol, 70 mM sucrose, 1 mM EGTA, and 5 mM HEPES, pH 7.2) using a ground-glass tissue homogenizer (KONTES, Vineland, N.J.). Protein content was measured using the Lowry method. Thirty micrograms of cellular lysate protein were loaded per lane and electrophoresed on SDS-PAGE (10% Bis-Tris gel:NuPAGE system, NOVEX, San Diego, Calif.) using 1× MES running buffer (50 mM MES, 50 mM Tris base, 0.5% SDS, 1.03 mM EDTA, pH 7.3). The proteins were then electroblotted onto nitrocellulose and probed with either ANT1 or ANT2 antisera using a KPL Western Blot Kit (Gaithersburg, Md.) and Amersham ECL® substrate (Arlington Hts., Ill.).

Example 4

Mouse pups or adults are treated with test compounds for metabolic therapy for energy deficiency or nucleic acid delivery systems for gene therapy (with a mouse-expressible Ant1 coding sequence) by a variety of route including, but not limited to oral or aerosol administration or injection intraperitoneally, intramuscularly or intravenously. Injection or alternate mode of administration depends on the particular therapeutic composition (compound or nucleic acid) being tested and whether the test animal is a pup or an adult. Formulations for test compositions and vectors for gene therapy are well understood and well known to the art.

Example 5
Evaluation of Test Compounds

By about six months of age the Ant1 (−/−) mice are detectably affected by the ANT1 deficiency. They are sacrificed and brain, heart, kidney, lung, hind-limb skeletal muscle and liver tissues are harvested and either frozen for histological analysis, activity staining, or fixed according to standard techniques for pathology and histological evaluation. Where desired, organ or tissue samples are frozen for subsequent DNA extraction and analysis.

In general, experiments are carried out with Ant1 (−/−) mice, starting at about 5–9 months of age, and the mice are weighed and divided into test and control groups. Test mice receive the compound for which evaluation as an antioxidant, bioenergetics modifier or as a gene therapy delivery system carrying the ANT1 cDNA or gene. Unless otherwise indicated, the test compound is administered in a pharmaceutically acceptable carrier by the appropriate route. Unless otherwise determined to be advantageous, the test compound is administered at the same time each day (±1 hour).

During the course of an experiment, each mouse is evaluated weekly for weight, lethargy, muscle weakness, breathing patterns, piloerection or other general signs of distress and for any indication of neurological and/or motor disorders (including for circling behavior, dystonia, trembling or the like). Blood or serum is monitored for lactic acid, alanine and Kreb cycle intermediates (for example succinate, citrate) in some experiments. Treated and untreated control animals are also tested for endurance (exercise stress) or ADP-stimulated respiration can be measured.

The ordinary skilled artisan understands that routes of administration other than intraperitoneal injection may be preferable or may facilitate experimental procedures for other potentially therapeutic compounds for use in the treatment of mitochondrial diseases or hyperproliferative cardiomyopathy tested in the present animal model system. The skilled artisan understands how to test a particular compound for its toxicity in a particular mammal, for its ability to cross the blood-brain barrier and for its ability to enter the bloodstream and/or the cerebrospinal fluid. Preferred compounds for metabolic therapy are those which readily enter circulation and the central nervous system so that maximum amelioration of any disorder or disease resulting from oxidative damage or chronic energy deficiency is effected. Optimal gene therapy delivery systems deliver the ANT1 cDNA gene to the appropriate target organ (e.g., skeletal muscle, heart, CNS, etc.).

TABLE 1

Respiration[1] of Isolated Mitochondria from Ant1[PGKneo] Mice

| Tissue | Genotype | Glutamate + Malate | | | | | Pyruvate + Malate | | | | | Succinate | | | | |
| --- | --- | --- | --- | --- | --- | --- | --- | --- | --- | --- | --- | --- | --- | --- | --- | --- |
| | | III[2] | IV[3] | RCR[4] | UC[5] | P/O[6] | III | IV | RCR | UC | P/O | III | IV | RCR | UC | P/O |
| Sk. Muscle | +/+ | 271.8 | 81.8 | 3.32 | 292.5 | 2.86 | 176.0 | 81.1 | 2.17 | 176.9 | 2.83 | 239.6 | 165.5 | 1.45 | 235.2 | 1.29 |
| | −/− | 86.8 | 75.8 | 1.15 | 142.9 | 2.17 | 99.3 | 92.5 | 1.07 | 166.1 | 2.17 | 164.7 | 164.7 | 1.00 | 290.6 | n.d[7] |
| Heart | +/+ | 296.2 | 91.4 | 3.24 | 312.8 | 2.52 | 173.2 | 71.4 | 2.43 | 163.9 | 2.55 | 322.9 | 230.4 | 1.40 | 464.4 | 1.52 |
| | −/− | 195.5 | 85.6 | 2.28 | n.d. | 2.62 | 149.9 | 60.3 | 2.49 | 155.3 | 2.50 | 342.3 | 228.2 | 1.50 | n.d. | 1.31 |
| Liver | +/+ | 129.0 | 29.5 | 4.37 | 129.1 | 2.54 | 59.4 | 23.8 | 2.50 | n.d. | 2.34 | 199.7 | 48.5 | 4.12 | 230.2 | 1.81 |
| | −/− | 128.1 | 34.0 | 3.78 | 139.8 | 2.72 | 69.9 | 23.3 | 3.00 | n.d. | 2.39 | 196.9 | 53.8 | 3.66 | n.d. | 1.81 |

[1]rates expressed as ng atom O/min/mg mitochondrial protein
[2]State III rate = ADP-stimulated rate
[3]State IV rate = ADP-limited rate
[4]Respiratory Control Ratio (RCR) = ratio of State III rate to State IV rate
[5]UC = Dinitrophenol (DNP)-uncoupled respiration rate
[6]P/O = ratio of ADP molecules phosphorylated to oxygen atoms reduced
[7]n.d. = not determined

TABLE 2

Blood levels of selected organic and amino acids in Ant1[PGKneo] mice

| | Genotypes | | | Published | |
|---|---|---|---|---|---|
| Organic acid | +/+ Pool[a] ($\mu$mol/L) | −/− Pool[a] ($\mu$mol/L) | Fold increase for −/− Pool | values for mice ($\mu$mol/L) | |
| Lactic acid | 1,974 | 8,295 | 4.20 | 1,588–1921 | |
| Pyruvic acid | 153 | 151 | 0.99 | n.a.[b] | |
| Succinic acid | 1 | 48 | 48 | n.a.[b] | |
| Citric acid | 132 | 228 | 1.73 | n.a.[b] | |
| Alanine | 614 | 953 | 1.55 | 595[c] | |

[a]n = 5.
[b]n.a. = not available
[c]Steel et al. (1950) Arch. Biochem. 25:124–132

We claim:

1. A transgenic Ant1 (−/−) mouse whose genome comprises disruption of the endogenous gene (Ant1) encoding the heart-muscle isoform of adenine nucleotide translocator protein, and wherein said disruption results in said mouse exhibiting chronic energy deprivation, muscle weakness and loss of strength and endurance, as compared to a wild-type mouse.

2. The mouse of claim 1, wherein the disruption of the Ant1 gene inactivates the Ant1 gene by the insertion of a selectable marker and a genetic marker whose expression is detected by histological staining.

3. The mouse of claim 2 wherein the selectable marker is a kanamycin resistance coding sequence and the marker whose expression is detected by histological staining is β-galactosidase.

4. A method for identifying a test composition which mitigates against fascioscapular humeral muscular dystrophy and/or mitochondrial myopathy and/or hypertrophic cardiomyopathy, said method comprising the steps of:

(a) administering a test composition to a transgenic Ant1 (−/−) mouse whose genome comprises disruption of the endogenous gene (Ant1) encoding the heart-muscle isoform of adenine nucleotide translocator protein, and wherein said disruption results in said mouse exhibiting chronic energy deprivation, muscle weakness and loss of strength and endurance, as compared to a wild-type mouse;

(b) measuring at least one parameter selected from the group consisting of heart size, ADP-stimulated respiration, exercise stress, resting lactic acid levels, lactate/pyruvate ratio, serum Kreb cycle intermediate or alanine levels, and performing histological examination of skeletal muscle tissue for mitochondrial abnormalities, mitochondrial proliferation, mitochondrial damage, mitochondrial DNA damage or red ragged fibers; and (c) comparing the parameter measured in step (b) with a corresponding measurement made of the same parameter made in a transgenic Ant1 (−/−) mouse to which the test composition has not been administered, whereby a test composition which mitigates against mitochondrial myopathy and/or hypertrophic cardiomyopathy is identified by lack of red ragged fibers, reduced hypertrophic cardiomyopathy, reduced mitochondrial myopathy, a normal lactic acid level, substantially normal serum alanine concentration, normal ADP-stimulated respiration, reduced mitochondrial proliferation, reduced mitochondrial DNA damage, reduced mitochondrial damage, or increased endurance as compared with an Ant1-deficient transgenic mouse to which the test composition was not administered.

5. The method of claim 4, wherein said test compound is a metabolic therapeutic compound.

6. The method of claim 4, wherein said test compound is a DNA construct having an Ant1 coding sequence.

7. A method for evaluating a test composition comprising a nucleic acid delivery system, wherein the target of said delivery system is heart and/or skeletal muscle, said method comprising the steps of:

(a) administering to a transgenic Ant1 (−/−) mouse whose genome comprises disruption of the endogenous gene (Ant1) encoding the heart-muscle isoform of adenine nucleotide translocator protein, and wherein said disruption results in said mouse exhibiting chronic energy deprivation, muscle weakness and loss of strength and endurance, as compared to a wild-type mouse a test composition;

(b) measuring at least one parameter selected from the group consisting of heart size, ADP-stimulated respiration, exercise stress, resting lactic acid level, lactate/pyruvate ratio, serum Kreb cycle intermediate and alanine levels or performing histological examination of skeletal muscle tissue for mitochondrial abnormalities, mitochondrial proliferation, mitochondrial DNA damage, or red ragged fibers; and (c) comparing the parameter measured or examination in step (b) with a corresponding measurement made in an Ant1 (+/+) mouse and to a measurement of the same parameter made in a transgenic Ant1 (−/−) mouse to which the test composition has not been administered, whereby a test composition comprising a nucleic acid delivery system effective for heart and/or skeletal muscle is identified by lack of red ragged fibers, reduced hypertrophic cardiomyopathy, reduced mitochondrial myopathy, reduced mitochondrial proliferation, reduced mitochondrial DNA damage, normal lactic acid level, substantially normal serum alanine concentration, normal ADP-stimulated respiration, or increased endurance as compared with an Ant1 (−/−) control transgenic mouse to which the test composition has not been administered.

8. Progeny of the transgenic mouse of claim 1, wherein the genome of a transgenic mouse of said progeny comprises a disruption of the endogenous Ant1 gene encoding the heart muscle isoform of adenine nucleotide translocator protein, wherein said disruption comprises the insertion of a selectable marker sequence, and wherein said disruption results in said mouse exhibiting chronic energy deprivation, muscle weakness, and loss of strength and endurance, as compared to a wild-type mouse.

* * * * *

UNITED STATES PATENT AND TRADEMARK OFFICE
CERTIFICATE OF CORRECTION

PATENT NO. : 6,013,858

DATED : January 11, 2000

INVENTOR(S) : Wallace et al.

It is certified that error appears in the above-identified patent and that said Letters Patent is hereby corrected as shown below:

In Column 2, line 37-38, after "heterozygous Ant1" please delete "(-/-)" and replace with --(+/-)--.
In Column 2, line 38, after "wild-type Ant1" please delete "(-/-)" and replace with --(+/+)--.
In Column 3, line 52, please delete "structdure" and replace with --structure--.
In Column 4, line 4, please delete "lactdic" and replace with --lactic--.
In Column 4, line 39, please delete "A=As1II" and replace with --AflI--.
In Column 4, line 39, please delete "S=SstII" and replace with --SstI--.
In Column 4, line 45, please delete "A=As1II" and replace with --AflII--
In Column 4, line 45, please delete "B=BstEII" and replace with --B=BglII--
In Column 4, line 56, please delete "color".
In Column 4, line 58, please delete "blue-".
In Column 4, line 64, please delete "blue" and replace with --stained--.
In Column 6, line 9, please delete "(FIG. 12)" and replace with --(FIG. 13)--.
In Column 6, line 48, please delete "(A in FIG. 5)" and replace with --(FIG. 5)--.
In Column 6, line 49-50, please delete "(B in FIG. 5)" and replace with --(FIG. 5)--.
In Column 7, line 35, please delete "(FIGS. 8A, 9A)" and replace with --(FIGS. 8B, 9B)--.
In Column 8, line 63, please delete "Ant1$^{PGKeno}$" and replace with --Ant1$^{PGKneo}$--.
In Column 10, line 33, please delete "Ant1$^{PGKeno}$" and replace with --Ant1$^{PGKneo}$--.
In Column 10, line 42, please delete "Ant1$^{PGKeno}$" and replace with --Ant1$^{PGKneo}$--.
In Column 12, line 43, please delete "Ant1$^{PGKeno}$" and replace with --Ant1$^{Kneo}$--.
In Column 14, line 55, please delete "ant1" and replace with --Ant1--.

Signed and Sealed this

Seventeenth Day of October, 2000

Q. TODD DICKINSON

*Attest:*

*Attesting Officer*      *Director of Patents and Trademarks*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 15 amino acids
      (B) TYPE: amino acid
      (C) STRANDEDNESS: single
      (D) TOPOLOGY: unknown (ii) MOLECULE TYPE: peptide (iii) HYPOTHETICAL: NO (xi) SEQUENCE DESCRIPTION: SEQ ID NO:1:

```
Met Gly Asp Gln Ala Leu Ser Phe Leu Lys Asp Phe Leu Ala Gly
1               5                   10                  15
```

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: unknown (ii) MOLECULE TYPE: peptide (iii) HYPOTHETICAL: NO (xi) SEQUENCE DESCRIPTION: SEQ ID NO:2:

```
Met Thr Asp Ala Ala Val Ser Phe Ala Lys Asp Phe Leu Ala Gly
1               5                   10                  15
```

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide."

(iii) HYPOTHETICAL: NO (xi) SEQUENCE DESCRIPTION: SEQ ID NO:3:

ATGATGATGC AGTCTGCCCC GGAAA                                                  25

(2) INFORMATION FOR SEQ ID NO:4:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:4:

GATCTCATCA TACAATACCA ATACA                                                  25

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:5:

AGGATTGGGA AGACAATAGC AGGC                                                   24

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:6:

GCCAGCAAAC AGATCAAGTG CAGAG                                                  25

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotide."

(iii) HYPOTHETICAL: NO (xi) SEQUENCE DESCRIPTION: SEQ ID NO:7:

TGAAGATCTT GGTGAGACAG TCGCC                                                  25

23

-continued

```
(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide."

(iii) HYPOTHETICAL: NO (xi) SEQUENCE DESCRIPTION: SEQ ID NO:8:

CCGTGCATCT GCCAGTTTGA GGGGA                                              25

(2) INFORMATION FOR SEQ ID NO:9:

(i) SEQUENCE CHARACTERISTICS:
        (A) LENGTH: 1177 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Mus musculus (ix) FEATURE:
        (A) NAME/KEY: CDS
        (B) LOCATION: 94..990

(xi) SEQUENCE DESCRIPTION: SEQ ID NO:9:

GCTGTCGACG CATTCGGGGT GGCGGTGCCT GGCCGGGCGT AGGCAAGAGC AAACGAGCGG          60

CTCCTTGCAG GCTGTGTGCG CCCGGCTTTC AGC ATG GGG GAT CAG GCT TTG AGC         114
                                     Met Gly Asp Gln Ala Leu Ser
                                       1               5

TTT CTT AAG GAC TTC CTG GCA GGT GGC ATC GCG GCC GCC GTC TCC AAG          162
Phe Leu Lys Asp Phe Leu Ala Gly Gly Ile Ala Ala Ala Val Ser Lys
         10                  15                  20

ACC GCG GTC GCC CCG ATC GAG AGG GTC AAA CTG CTG CTG CAG GTC CAG          210
Thr Ala Val Ala Pro Ile Glu Arg Val Lys Leu Leu Leu Gln Val Gln
 25                  30                  35

CAT GCC AGC AAA CAG ATC AGT GCA GAG AAG CAG TAC AAA GGC ATC ATT          258
His Ala Ser Lys Gln Ile Ser Ala Glu Lys Gln Tyr Lys Gly Ile Ile
 40                  45                  50                  55

GAT TGT GTC GTG AGA ATC CCC AAG GAG CAG GGC TTT CTC TCT TTC TGG          306
Asp Cys Val Val Arg Ile Pro Lys Glu Gln Gly Phe Leu Ser Phe Trp
                 60                  65                  70

AGG GGT AAC CTG GCC AAC GTG ATC CGG TAC TTC CCC ACT CAA GCC CTG          354
Arg Gly Asn Leu Ala Asn Val Ile Arg Tyr Phe Pro Thr Gln Ala Leu
             75                  80                  85

AAC TTC GCC TTC AAA GAC AAG TAC AAG CAG ATC TTC CTG GGA GGC GTT          402
Asn Phe Ala Phe Lys Asp Lys Tyr Lys Gln Ile Phe Leu Gly Gly Val
         90                  95                 100

GAT CGA CAT AAG CAG TTC TGG CGC TAC TTT GCT GGT AAC CTG GCC TCT          450
Asp Arg His Lys Gln Phe Trp Arg Tyr Phe Ala Gly Asn Leu Ala Ser
    105                 110                 115

GGT GGG GCA GCT GGG GCC ACC TCC CTC TGC TTC GTC TAC CCG CTG GAC          498
Gly Gly Ala Ala Gly Ala Thr Ser Leu Cys Phe Val Tyr Pro Leu Asp
120                 125                 130                 135

TTT GCT AGG ACC ACG CTG GCT GCG GAC GTG GGC AAG GGA TCT TCC CAG          546
Phe Ala Arg Thr Thr Leu Ala Ala Asp Val Gly Lys Gly Ser Ser Gln
                140                 145                 150
```

```
CGA GAA TTC AAT GGG CTG GGC GAC TGT CTC ACC AAG ATC TTC AAG TCG     594
Arg Glu Phe Asn Gly Leu Gly Asp Cys Leu Thr Lys Ile Phe Lys Ser
            155                 160                 165

GAC GGC CTG AAG GGT CTC TAC CAG GGT TTC AGT GTC TCT GTC CAG GGC     642
Asp Gly Leu Lys Gly Leu Tyr Gln Gly Phe Ser Val Ser Val Gln Gly
            170                 175                 180

ATC ATC ATC TAC AGA GCT GCC TAC TTC GGA GTC TAT GAC ACT GCC AAG     690
Ile Ile Ile Tyr Arg Ala Ala Tyr Phe Gly Val Tyr Asp Thr Ala Lys
185                 190                 195

GGG ATG CTG CCA GAC CCC AAG AAT GTG CAC ATT ATC GTG AGC TGG ATG     738
Gly Met Leu Pro Asp Pro Lys Asn Val His Ile Ile Val Ser Trp Met
200                 205                 210                 215

ATT GCC CAG AGT GTG ACA GCC GTT GCG GGG CTG GTG TCT TAT CCG TTT     786
Ile Ala Gln Ser Val Thr Ala Val Ala Gly Leu Val Ser Tyr Pro Phe
            220                 225                 230

GAC ACT GTT CGT CGT AGG ATG ATG ATG CAG TCT GGC CGC AAA GGG GCT     834
Asp Thr Val Arg Arg Arg Met Met Met Gln Ser Gly Arg Lys Gly Ala
            235                 240                 245

GAT ATT ATG TAC ACG GGG ACA CTT GAC TGC TGG AGG AAG ATT GCA AAA     882
Asp Ile Met Tyr Thr Gly Thr Leu Asp Cys Trp Arg Lys Ile Ala Lys
            250                 255                 260

GAT GAA GGA GCC AAC GCT TTC TTC AAA GGT GCT TGG TCC AAT GTA CTG     930
Asp Glu Gly Ala Asn Ala Phe Phe Lys Gly Ala Trp Ser Asn Val Leu
265                 270                 275

AGA GGC ATG GGT GGT GCT TTT GTA TTG GTA TTG TAT GAT GAG ATC AAA     978
Arg Gly Met Gly Gly Ala Phe Val Leu Val Leu Tyr Asp Glu Ile Lys
280                 285                 290                 295

AAA TAT GTG TAA TACCCAAGCT CACAAGTTCA CAGATCCATT GTGTGGTTTA        1030
Lys Tyr Val *

ACACACTATT CTTGAGGAAA TAAAACAAAA AAAAGAGACA GATCTTGGAT AAAACCAGAC   1090

CGTAAGGAAT ACCTCAGAAA AAAATGCTTC ATTGAGTATT CATTAAACCA CAGAAGTATT   1150

TTCTATTTAT TTTACATTTA GATTCCC                                     1177

(2) INFORMATION FOR SEQ ID NO:10:

(i) SEQUENCE CHARACTERISTICS:
        (A) LENGTH:  298 amino acids
        (B) TYPE: amino acid
        (D) TOPOLOGY: linear (ii) MOLECULE TYPE: protein (xi) SEQUENCE DESCRIPTION: SEQ ID NO:10:

Met Gly Asp Gln Ala Leu Ser Phe Leu Lys Asp Phe Leu Ala Gly Gly
 1               5                  10                  15

Ile Ala Ala Ala Val Ser Lys Thr Ala Val Ala Pro Ile Glu Arg Val
                20                  25                  30

Lys Leu Leu Leu Gln Val Gln His Ala Ser Lys Gln Ile Ser Ala Glu
            35                  40                  45

Lys Gln Tyr Lys Gly Ile Ile Asp Cys Val Val Arg Ile Pro Lys Glu
        50                  55                  60

Gln Gly Phe Leu Ser Phe Trp Arg Gly Asn Leu Ala Asn Val Ile Arg
65                  70                  75                  80

Tyr Phe Pro Thr Gln Ala Leu Asn Phe Ala Phe Lys Asp Lys Tyr Lys
                85                  90                  95

Gln Ile Phe Leu Gly Gly Val Asp Arg His Lys Gln Phe Trp Arg Tyr
            100                 105                 110
```

```
Phe Ala Gly Asn Leu Ala Ser Gly Gly Ala Ala Gly Ala Thr Ser Leu
            115                 120                 125

Cys Phe Val Tyr Pro Leu Asp Phe Ala Arg Thr Thr Leu Ala Ala Asp
130                 135                 140

Val Gly Lys Gly Ser Ser Gln Arg Glu Phe Asn Gly Leu Gly Asp Cys
145                 150                 155                 160

Leu Thr Lys Ile Phe Lys Ser Asp Gly Leu Lys Gly Leu Tyr Gln Gly
                165                 170                 175

Phe Ser Val Ser Val Gln Gly Ile Ile Ile Tyr Arg Ala Ala Tyr Phe
            180                 185                 190

Gly Val Tyr Asp Thr Ala Lys Gly Met Leu Pro Asp Pro Lys Asn Val
            195                 200                 205

His Ile Ile Val Ser Trp Met Ile Ala Gln Ser Val Thr Ala Val Ala
            210                 215                 220

Gly Leu Val Ser Tyr Pro Phe Asp Thr Val Arg Arg Arg Met Met Met
225                 230                 235                 240

Gln Ser Gly Arg Lys Gly Ala Asp Ile Met Tyr Thr Gly Thr Leu Asp
                245                 250                 255

Cys Trp Arg Lys Ile Ala Lys Asp Glu Gly Ala Asn Ala Phe Phe Lys
            260                 265                 270

Gly Ala Trp Ser Asn Val Leu Arg Gly Met Gly Gly Ala Phe Val Leu
            275                 280                 285

Val Leu Tyr Asp Glu Ile Lys Lys Tyr Val
290                 295
```

(2) INFORMATION FOR SEQ ID NO:11:

(i) SEQUENCE CHARACTERISTICS:
        (A) LENGTH: 1259 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (ix) FEATURE:
        (A) NAME/KEY: CDS
        (B) LOCATION: 190..1086

(xi) SEQUENCE DESCRIPTION: SEQ ID NO:11:

```
ATTCCCACCA CCGAATAAAC CTCNCTTNNG GGGNCCCCAA NTTGAGCMCC CCCCCGGKGG      60

SSGNCTNSYC NRANRMNADN KGNNCCTYCS NGKCNTNNAN GGNACAGAHN NSSGGNGNNG     120

GTNCCTGNCC GGGCGTAGVC NANAVCAAAC GANCGNCTCC NTKNAGGCTG TGTGCGCCCG     180

GCTTTCAGCA TGGGGGATCA GGCTTTGAGC TTTCTTAAGG ACTTCCTGGC AGGTGGCATC     240

GCCGCCGCCG TCTCCAAGAC GGCGGTCGCC CCGATCGAGA GGGTCAAACT GCTGCTGCAG     300

GTCCAGCATG CCAGCAAACA GATCAGTGCA GAGAAGCAGT ACAAAGGCAT CATTGATTGT     360

GTCGTGAGAA TCCCCAAGGA GCAGGGCTTT CTCTCTTTCT GGAGGGGTAA CCTGGCCAAC     420

GTGATCCGGT ACTTCCCCAC TCAAGCCCTG AACTTCGCCT TCAAAGACAA GTACAAGCAG     480

ATCTTCCTGG GAGGCGTGGA TCGCCATAAG CAGTTCTGGC GCTACTTTGC TGGTAACCTG     540

GCCTCTGGTG GGGCAGCTGG GGCCACCTCC CTCTGCTTCG TCTACCCGCT GGACTTTGCT     600

AGGACCAGGC TGGCTGCCGA CGTGGGCAAG GGATCTTCCC AGCGAGAATT CAATGGGCTG     660

GGCGACTGTC TCACCAAGAT CTTCAAGTCG GACGGCCTGA CGGGTCTCTA CCAGGGTTTC     720

AGTGTCTCTG TCCAGGGCAT CATCATCTAC AGAGCTGCCT ACTTCGGAGT CTATGACACT     780
```

-continued

```
GCCAAGGGGA TGCTGCCAGA CCCCAAGAAT GTGCACATTA TCGTGAGCTG GATGATTGCC      840

CAGAGTGTGA CAACGGTGGC GGGGCTGGTG TCCTATCCGT TTGACACTGT TCGTCGTAGG      900

ATGATGATGC AGTCTGCCCG CAAAGGGGCT GATATTATGT ACACGGGGAC ACTTGACTGC      960

TGGAGGAAGA TTGCAAAAGA TGAAGGAGCC AACGCTTTCT TCAAAGGTGC TTGGTCCAAT     1020

GTACTGAGAG GCATGGGTGG TGCTTTTGTA TTGGTATTGT ATGATGAGAT CAAAAAATAT     1080

GTGTAATACC CAAGCTCACA AGTTCACAGA TCCATTGTGT GGTTTAACAG ACTATTCTTG     1140

AGGAAATAAA AMANRCANAC NCANAAKAGA CNGATCTTGG ATAMNACCAN ACCGTAAGGA     1200

ATACCKSGGA ATTCGATATC GAGCTTATCC ATACCGTCGA CCTCGAGGGG GGGCCCGGT     1259
```